US011725227B2

(12) United States Patent
Chou et al.

(10) Patent No.: US 11,725,227 B2
(45) Date of Patent: Aug. 15, 2023

(54) DEVICES AND METHODS FOR EXAMINING DRUG EFFECTS ON MICROORGANISMS

(71) Applicant: Essenlix Corporation, Monmouth Junction, NJ (US)

(72) Inventors: Stephen Y. Chou, Princeton, NJ (US); Wei Ding, Princeton, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 0 days.

(21) Appl. No.: 16/640,254

(22) PCT Filed: Aug. 1, 2018

(86) PCT No.: PCT/US2018/044795
§ 371 (c)(1),
(2) Date: Feb. 19, 2020

(87) PCT Pub. No.: WO2019/028133
PCT Pub. Date: Feb. 7, 2019

(65) Prior Publication Data
US 2020/0399675 A1 Dec. 24, 2020

Related U.S. Application Data

(60) Provisional application No. 62/539,677, filed on Aug. 1, 2017.

(51) Int. Cl.
| | | |
|---|---|---|
| *C12Q 1/18* | (2006.01) | |
| *G16H 40/67* | (2018.01) | |
| *G16H 10/40* | (2018.01) | |
| *G16H 30/40* | (2018.01) | |
| *G16H 80/00* | (2018.01) | |
| *C12M 1/34* | (2006.01) | |
| *G01N 1/30* | (2006.01) | |
| *G06T 7/00* | (2017.01) | |

(52) U.S. Cl.
CPC ............ *C12Q 1/18* (2013.01); *C12M 41/46* (2013.01); *G01N 1/30* (2013.01); *G06T 7/0016* (2013.01); *G16H 10/40* (2018.01); *G16H 30/40* (2018.01); *G16H 40/67* (2018.01); *G16H 80/00* (2018.01); *G06T 2207/10016* (2013.01); *G06T 2207/30024* (2013.01)

(58) Field of Classification Search
None
See application file for complete search history.

(56) References Cited

U.S. PATENT DOCUMENTS

| | | |
|---|---|---|
| 3,368,872 A | 2/1968 | Natelson |
| 3,447,863 A | 6/1969 | Patterson |
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |

(Continued)

FOREIGN PATENT DOCUMENTS

| | | |
|---|---|---|
| AU | 1378988 A | 9/1988 |
| AU | 619459 B | 1/1992 |

(Continued)

OTHER PUBLICATIONS

Van Vliet, Dillys et al., Prediction of asthma exacerbations in children by innovative exhaled inflammatory markers: Results of a longitudinal study, Plos One, Mar. 23, 2015, vol. 10. No. 3, e0119434.

International Report on Patentability for PCT/US2018/037168 established by IPEA/US dated Aug. 19, 2019.

Sun, W., et al. Rapid antimicrobial susceptibility test for identification of new therapeutics and drug combinations against multidrug-resistant bacteria, Emerg Microbes Infect Nov. 9, 2016;5(11):e116 doi: 10.1038/emi.2016.123.

(Continued)

*Primary Examiner* — Vera Afremova

(57) ABSTRACT

The present invention provides devices, systems, and methods, for performing biological and chemical assays.

49 Claims, 4 Drawing Sheets

(56) References Cited

U.S. PATENT DOCUMENTS

| | | |
|---|---|---|
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Levine et al. |
| 6,016,367 A | 1/2000 | Benedetti et al. |
| 6,017,767 A | 1/2000 | Chandler |
| 6,022,734 A | 2/2000 | Wardlaw |
| 6,083,761 A | 7/2000 | Kedar et al. |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Levine et al. |
| 9,023,641 B2 | 5/2015 | Rodriguez et al. |
| 9,044,268 B2 | 6/2015 | Phillips et al. |
| 9,046,473 B2 | 6/2015 | Levine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,657,327 B2 * | 5/2017 | Metzger .................. C12Q 1/18 |
| 9,696,252 B2 | 7/2017 | Wardlaw |
| 10,605,805 B2 * | 3/2020 | Chou .................. G16H 80/00 |
| 2001/0055882 A1 | 12/2001 | Ostuni |
| 2002/0164820 A1 | 11/2002 | Brown |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |

(56) References Cited

U.S. PATENT DOCUMENTS

| | | |
|---|---|---|
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0212462 A1 | 9/2011 | Duffy et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2012/0321518 A1 | 12/2012 | Ermantraut et al. |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0252847 A1 | 9/2013 | Mckenna et al. |
| 2013/0265054 A1 | 10/2013 | Lowery et al. |
| 2013/0309679 A1 | 11/2013 | Ismagilov et al. |
| 2014/0273272 A1 | 9/2014 | Gayda et al. |
| 2014/0315242 A1 | 10/2014 | Rodriguez et al. |
| 2014/0323330 A1 | 10/2014 | Bergo |
| 2014/0368631 A1 | 12/2014 | Wardlaw et al. |
| 2014/0378320 A1 | 12/2014 | Hoffmann et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | |
|---|---|---|
| CN | 1299466 A | 6/2001 |
| CN | 1302229 A | 7/2001 |
| CN | 1166950 C | 9/2004 |
| CN | 1188217 C | 2/2005 |
| CN | 102027369 | 4/2011 |
| EP | 261667 A2 | 3/1988 |
| EP | 291153 A1 | 11/1988 |
| EP | 261667 A3 | 5/1989 |
| EP | 291153 B1 | 6/1992 |
| EP | 261667 B1 | 2/1993 |
| EP | 0961110 | 12/1999 |
| EP | 1949310 A2 | 7/2008 |
| EP | 2290100 | 3/2011 |
| EP | 1949310 A4 | 11/2011 |
| EP | 2439515 | 4/2012 |
| EP | 2554987 | 2/2013 |
| EP | 3026433 | 6/2016 |
| EP | 1949310 B1 | 2/2019 |
| WO | 1991020009 | 12/1991 |
| WO | 1999044743 | 9/1999 |
| WO | 1999045385 | 9/1999 |
| WO | 2003062920 | 7/2003 |
| WO | 2005114145 | 12/2005 |
| WO | 2005100539 | 1/2006 |
| WO | 2007112332 | 10/2007 |
| WO | 2009117652 | 9/2009 |
| WO | 2009117664 | 9/2009 |
| WO | 2009117678 | 9/2009 |
| WO | 2009117682 | 9/2009 |
| WO | 2009124186 | 10/2009 |
| WO | 2009124190 | 10/2009 |
| WO | 2009126800 | 10/2009 |
| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2016081941 A1 | 5/2016 |
| WO | WO 2017/048871 * | 3/2017 |

OTHER PUBLICATIONS

International Preliminary Report on Patentability for the corresponding PCT/US2018/044795 established by IPEA/US dated Oct. 17, 2018.

International Search Report and Written Opinion of the International Searching Authority for the corresponding PCT/US2018/044795 dated Apr. 2, 2020.

* cited by examiner

DEVICES AND METHODS FOR EXAMINING DRUG EFFECTS ON MICROORGANISMS

CROSS-REFERENCE

This application is a National Stage entry (§ 371) application of International Application No. PCT/US2018/044795, filed on Aug. 1, 2018, which claims the benefit of U.S. Provisional Patent Application No. 62/539,677, filed Aug. 1, 2017, the contents of which are relied upon and incorporated herein by reference in their entirety.

The entire disclosure of any publication or patent document mentioned herein is entirely incorporated by reference.

FIELD

Among other things, the present invention is related to devices and methods of performing biological and chemical assays, in particular, of microorganisms.

BACKGROUND

In diagnostic and clinical settings, it is often necessary to examine drug effects on microorganisms. For instance, susceptibility tests, which determine which antimicrobials will inhibit the growth of the bacteria or fungi causing a specific infection in a patient, are often used to help health practitioners determine which drugs or therapeutic strategies will be most effective in treating the patient's infection. However, in reality, such tests are usually laborious, time-consuming, and require sophisticated laboratory settings and professional handling. Particularly, conventional methods that typically involve growing a culture of the infection site and monitoring the growth of the culture over time after application of the antimicrobials cost an undesirably long time in the face of, very often, swiftly-developing or even life-threatening infections. It is therefore well recognized in the art that a fast, easy-to-handle, and accurate substitute test is desirable.

The present invention provides devices and methods to tackle the foregoing problems in examining drug effects on microorganisms.

One aspect of the present invention uses (a) two plates to compress a sample that comprises the microorganisms to be examined into a thin layer, and (b) after (a), an imaging process to count and/or track the microorganisms over a time period or at discrete time points.

Another aspect of the present invention uses spacers to control the final sample thickness and hence to assist a determination of the microorganism concentration.

Yet another aspect of the present invention provides that the drugs to be examined are coated on one or both of the plates, in that the coated drugs are capable of, upon contacting the sample, being dissolved and diffuse in the sample.

Yet another aspect of the present invention provides multiplexing capabilities for the drug effect examination with the two plates and drugs coated at different locations on the plate(s).

Yet another aspect of the present invention uses a cell viability dye that is added to the sample when the sample is being loaded between the provided two plates and monitoring the microorganism viability with the aid of the dye.

Yet another aspect of the present invention provides the use of mobile communication device, for instance, a cell phone, for the imaging of the microorganisms loaded between the provided two plates.

Yet another aspect of the present invention uses the mobile communication device for, in addition to imaging, communicating the test results with health professional or other parties.

BRIEF DESCRIPTION OF THE DRAWINGS

The skilled artisan will understand that the drawings, described below, are for illustration purposes only. The drawings are not intended to limit the scope of the present teachings in any way. Some of the drawings are not in scale. In the figures that present experimental data points, the lines that connect the data points are for guiding a viewing of the data only and have no other means.

DETAILED DESCRIPTION OF EXEMPLARY EMBODIMENTS

Figure 1:
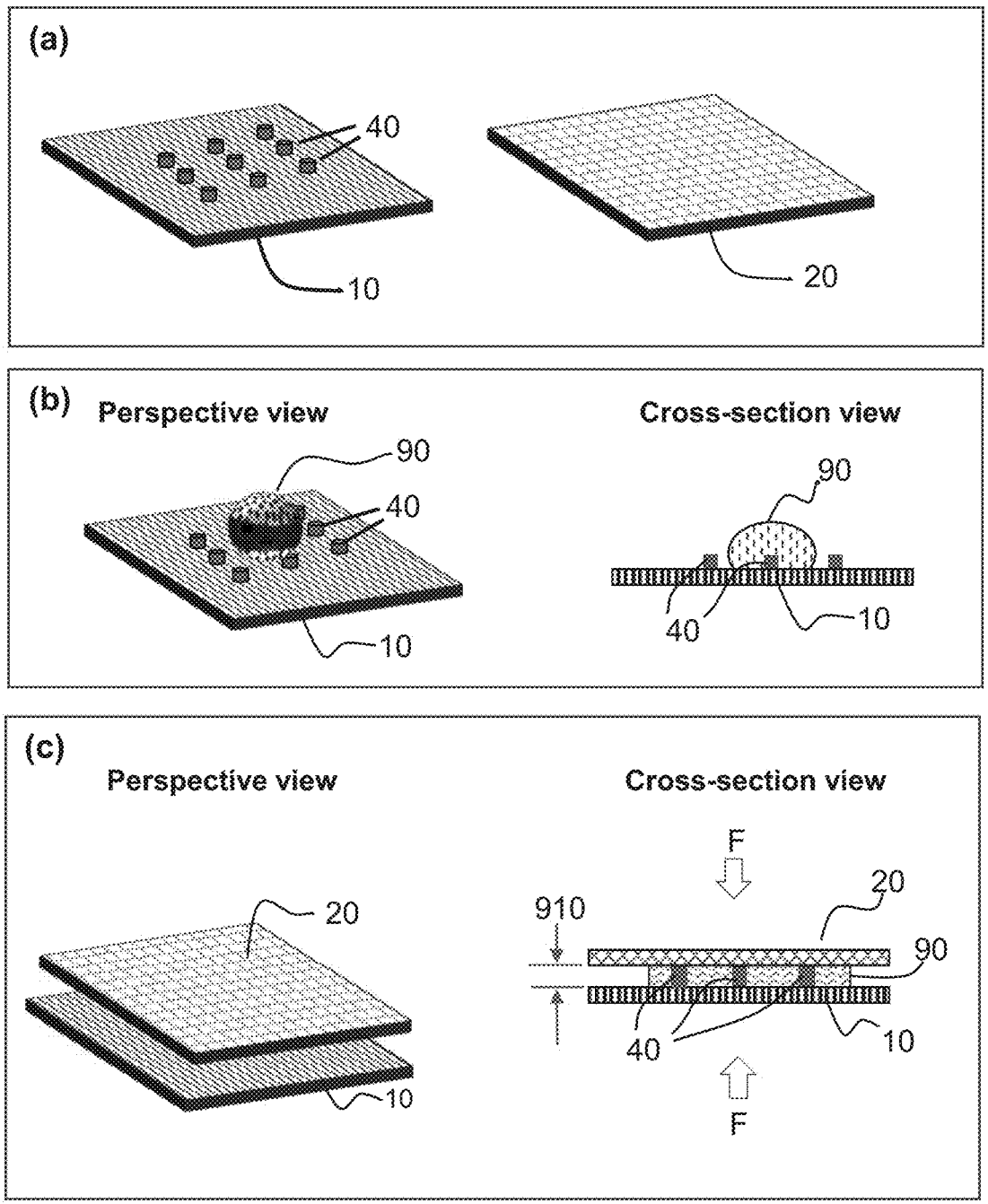
FIG. 1 shows an embodiment of a generic QMAX (Q: quantification; M: magnifying; A: adding reagents; X: acceleration; also known as compressed regulated open flow (CROF)) device.

The following detailed description illustrates some embodiments of the invention by way of example and not by way of limitation. If any, the section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

Among other things, the present invention provides devices, systems, and methods of performing biological and chemical assays using a QMAX card.

The exemplary embodiments herein disclosed can be combined with the bio/chemical devices and assays including, but not limited to, the devices and assays as disclosed, described, and/or referred to in the following applications:

PCT Application No. PCT/US2016/045437, which was filed on Aug. 10, 2016,

PCT Application No. PCT/US2016/051775, which was filed on Sep. 14, 2016,

PCT Application No. PCT/US2016/051794, which was filed on Sep. 14, 2016,

U.S. Provisional Application No. 62/369,181, which was filed on Jul. 31, 2016,

U.S. Provisional Application No. 62/412,006, which was filed on Oct. 24, 2016,

U.S. Provisional Application No. 62/437,339, which was filed on Dec. 21, 2016,

U.S. Provisional Application No. 62/431,639, which was filed on Dec. 9, 2016,
U.S. Provisional Application No. 62/456,065, which was filed on Feb. 7, 2017,
U.S. Provisional Application No. 62/456,488, which was filed on Feb. 8, 2017,
U.S. Provisional Application No. 62/456,287, which was filed on Feb. 8, 2017,
U.S. Provisional Application No. 62/456,528, which was filed on Feb. 8, 2017,
U.S. Provisional Application No. 62/456,537, which was filed on Feb. 8, 2017,
U.S. Provisional Application No. 62/456,612, which was filed on Feb. 8, 2017,
U.S. Provisional Application No. 62/456,631, which was filed on Feb. 8, 2017,
U.S. Provisional Application No. 62/456,596, which was filed on Feb. 8, 2017,
U.S. Provisional Application No. 62/456,590, which was filed on Feb. 8, 2017,
U.S. Provisional Application No. 62/456,638, which was filed on Feb. 8, 2017,
U.S. Provisional Application No. 62/456,598, which was filed on Feb. 8, 2017,
U.S. Provisional Application No. 62/456,552, which was filed on Feb. 8, 2017,
U.S. Provisional Application No. 62/456,603, which was filed on Feb. 8, 2017,
U.S. Provisional Application No. 62/456,585, which was filed on Feb. 8, 2017,
U.S. Provisional Application No. 62/456,628, which was filed on Feb. 8, 2017,
U.S. Provisional Application No. 62/456,504, which was filed on Feb. 8, 2017,
U.S. Provisional Application No. 62/456,988, which was filed on Feb. 9, 2017,
U.S. Provisional Application No. 62/457,084, which was filed on Feb. 9, 2017,
U.S. Provisional Application No. 62/457,031, which was filed on Feb. 9, 2017,
U.S. Provisional Application No. 62/456,904, which was filed on Feb. 9, 2017,
U.S. Provisional Application No. 62/457,075, which was filed on Feb. 9, 2017,
U.S. Provisional Application No. 62/457,009, which was filed on Feb. 9, 2017,
U.S. Provisional Application No. 62/457,133, which was filed on Feb. 9, 2017,
U.S. Provisional Application No. 62/457,103, which was filed on Feb. 9, 2017,
U.S. Provisional Application No. 62/459,267, which was filed on Feb. 15, 2017,
U.S. Provisional Application No. 62/459,303, which was filed on Feb. 15, 2017,
U.S. Provisional Application No. 62/459,337, which was filed on Feb. 15, 2017,
U.S. Provisional Application No. 62/459,232, which was filed on Feb. 15, 2017,
U.S. Provisional Application No. 62/459,160, which was filed on Feb. 15, 2017,
U.S. Provisional Application No. 62/459,972, which was filed on Feb. 16, 2017,
U.S. Provisional Application No. 62/394,753, which was filed on Sep. 15, 2016,
U.S. Provisional Application No. 62/459,496, which was filed on Feb. 15, 2017,
U.S. Provisional Application No. 62/459,554, which was filed on Feb. 15, 2017,
U.S. Provisional Application No. 62/460,047, which was filed on Feb. 16, 2017,
U.S. Provisional Application No. 62/459,598, which was filed on Feb. 15, 2017,
U.S. Provisional Application No. 62/460,083, which was filed on Feb. 16, 2017,
U.S. Provisional Application No. 62/460,076, which was filed on Feb. 16, 2017,
U.S. Provisional Application No. 62/460,062, which was filed on Feb. 16, 2017,
U.S. Provisional Application No. 62/459,920, which was filed on Feb. 16, 2016,
U.S. Provisional Application No. 62/459,577, which was filed on Feb. 15, 2017,
U.S. Provisional Application No. 62/459,602, which was filed on Feb. 15, 2017,
U.S. Provisional Application No. 62/460,069, which was filed on Feb. 16, 2017,
U.S. Provisional Application No. 62/460,088, which was filed on Feb. 16, 2017,
U.S. Provisional Application No. 62/460,091, which was filed on Feb. 16, 2017,
U.S. Provisional Application No. 62/460,757, which was filed on Feb. 18, 2017,
U.S. Provisional Application No. 62/463,578, which was filed on Feb. 24, 2017, which are all hereby incorporated in reference by their entireties.

The embodiments in these applications herein incorporated can be regarded in combination with one another or as a single invention, rather than as discrete and independent filings. Moreover, the exemplary embodiments disclosed herein are applicable to embodiments including but not limited to: bio/chemical assays, QMAX cards and systems, QMAX with hinges, notches, recessed edges and sliders, assays and devices with uniform sample thickness, smartphone detection systems, cloud computing designs, various detection methods, labels, capture agents and detection agents, analytes, diseases, applications, and samples; the various embodiments are disclosed, described, and/or referred to in the aforementioned applications, all of which are hereby incorporated in reference by their entireties.

The term "microorganism" as used herein refers to any organism that is small in size and can only be visualized through the aid of a microscope, typically with an average dimension less than 1 mm. Microorganisms as used herein include, but not limited to, bacteria, fungi, archaea, viruses, protists, and micro-animals (like myxozoa, arthropods, crustaceans, and microscopic nematodes).

The terms "drug" and "test reagent" as used herein are inter-changeable and refer to a bio/chemical reagent whose effects on one or many microorganisms are to be examined. The term "antimicrobial" or "antimicrobial reagent" refers to a bio/chemical reagent that is capable of inhibiting the survival or growth of one or many microorganisms.

The terms "proliferate (proliferation)" and "divide (division)" as used herein with a microorganism(s) as subject thereof are inter-changeable and refer to the action/process the microorganism individual takes to produce new individual through dividing the parent individual cell into two or more daughter cells, resulting in an increase in the number of the subject microorganism individuals.

QMAX Device

FIG. 1 shows an embodiment of a generic QMAX (Q: quantification; M: magnifying; A: adding reagents; X: acceleration; also known as compressed regulated open flow (CROF)) device. The generic QMAX device comprises a first plate 10 and a second plate 2. In particular, panel (A) shows the perspective view of a first plate 10 and a second plate 20 wherein the first plate has spacers. It should be noted, however, that the spacers can also be fixed on the second plate 20 (not shown) or on both first plate 10 and second plate 20 (not shown). Panel (B) shows the perspective view and a sectional view of depositing a sample 90 on the first plate 10 at an open configuration. It should be noted, however, that the sample 90 also can also be deposited on the second plate 20 (not shown), or on both the first plate 10 and the second plate 20 (not shown). Panel (C) illustrates (i) using the first plate 10 and second plate 20 to spread the sample 90 (the sample flow between the inner surfaces of the plates) and reduce the sample thickness, and (ii) using the spacers and the plate to regulate the sample thickness at the closed configuration of the QMAX device. The inner surfaces of each plate have one or a plurality of binding sites and or storage sites (not shown). In some embodiments, the spacers 40 have a predetermined uniform height and a predetermined uniform inter-spacer distance. In the closed configuration, as shown in panel (C) of FIG. 1, the spacing between the plates and the thus the thickness of the sample 90 is regulated by the spacers 40. In some embodiments, the uniform thickness of the sample 90 is substantially similar to the uniform height of the spacers 40. It should be noted that although FIG. 1 shows the spacers 40 to be fixed on one of the plates, in some embodiments the spacers are not fixed. For example, in certain embodiments the spacers are mixed with the sample so that when the sample is compressed into a thin layer, the spacers, which is rigid beads or particles that have a uniform size, regulate the thickness of the sample layer.

Monitoring of the Microorganisms

Common antimicrobial reagents effect on microorganism, e.g. bacteria or fungi, through inhibiting the cell proliferation process (e.g. "bacteriostatic"), or directly killing the cells (e.g. "bactericidal") via processes like destroying the integrity of the cell wall or cell membrane, etc. For instance, penicillins and cephalosporins have bactericidal effects by targeting the bacterial cell wall, while tetracyclines are protein synthesis inhibitor that blocks bacterial division. Other reagents may effect on microorganisms via similar mechanisms, or in the opposite direction, promote the viability and/or proliferation of the microorganisms. To examine the drug effects on microorganisms involves mainly the monitoring of one or many aspects of the microorganisms after the application of the test reagent, such as, but not limited to, number of the microorganisms resulting from the cell proliferation or cell death, proliferation speed, cell motility, cell morphology, cell membrane permeability, cell respiration.

Figure 2:
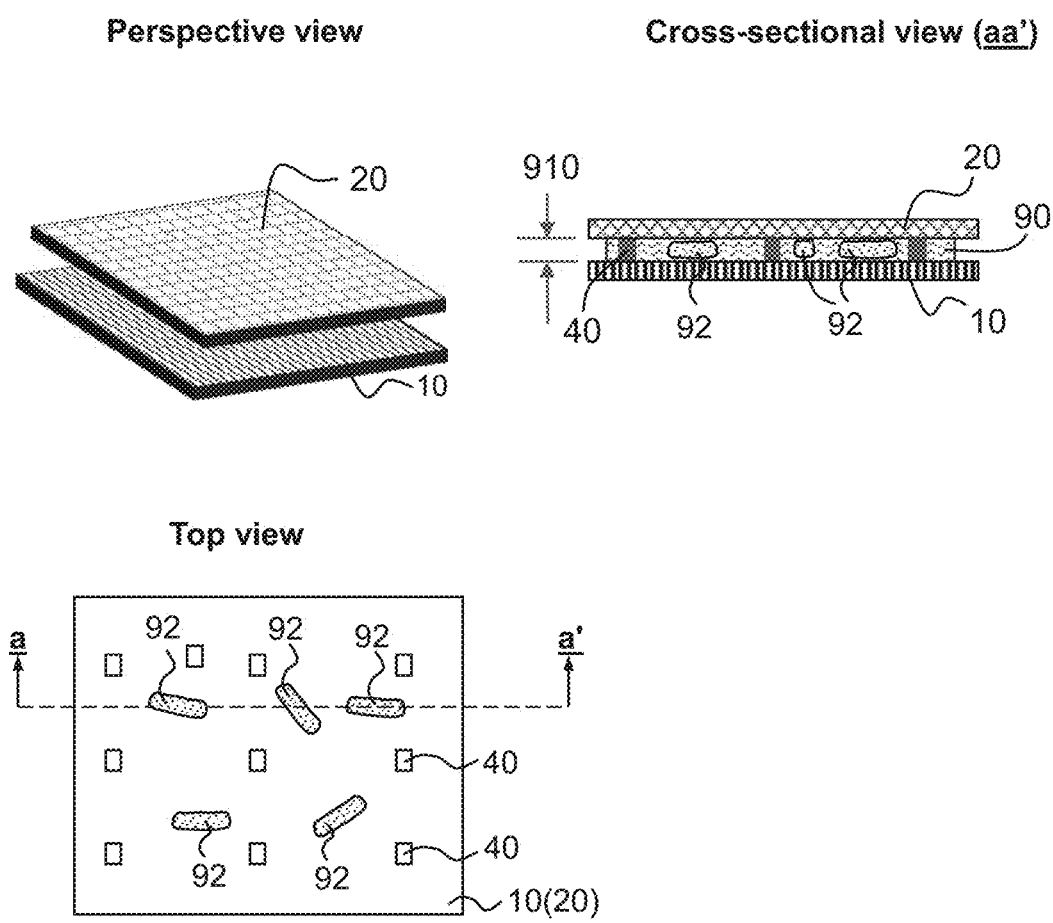
FIG. 2 shows one exemplary embodiment of the present invention, in which a QMAX device is used to monitor microorganisms.

It is one aspect of the present invention to use a QMAX device to monitor microorganisms via one or many approaches. FIG. 2 shows one exemplary embodiment of the present invention, in which a QMAX device is used to monitor microorganisms. A perspective view, a top view, and a cross-sectional view taken at line aa' of the QMAX device with a deposited sample are shown, respectively. The QMAX device comprises a first plate 10, a second plate 20, and spacers, and, as depicted, is at its closed configuration. In the closed configuration, a sample 90 that comprises microorganisms 92 to be analyzed is confined by the two plates into a thin layer. The thickness of the thin layer 901 is regulated by the two plates and the spacers 40. In this exemplary embodiment, the thin layer thickness 901 is equal to the spacer height, which is selected such that the microorganisms 92 are confined into a single layer between the plates without being compressed. As such, the microorganisms 92 are ready to be visualized and monitored by one or many approaches, depending on the suspected effects of the test reagent on the microorganisms that are to be analyzed. Below we discuss some exemplary aspects of the microorganisms to be monitored under the influence of the test reagent(s).

Figure 3:
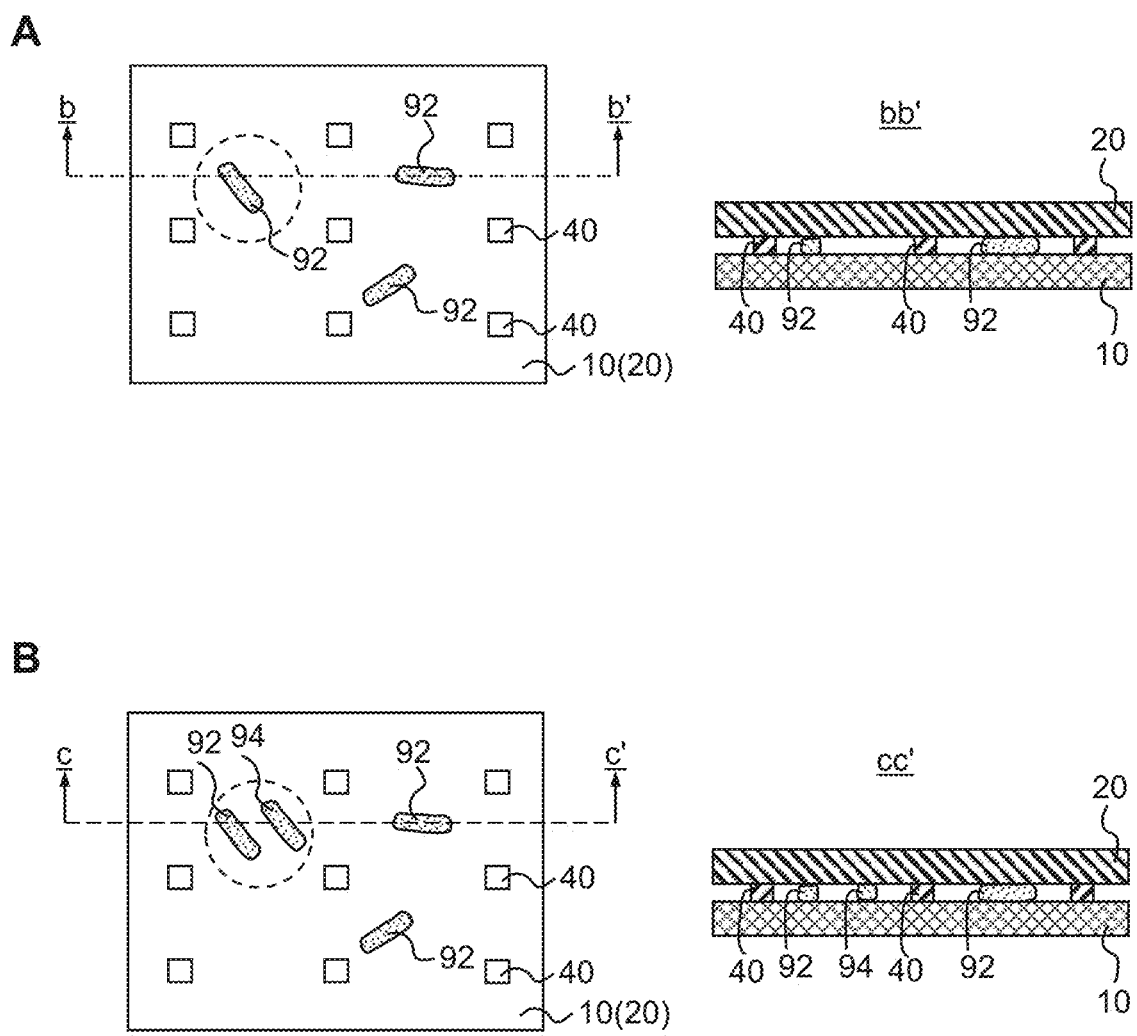
FIG. 3 shows one exemplary embodiment of the present invention whereby the microorganisms to be monitored proliferate between the two plates.

FIG. 3 shows one exemplary embodiment of the present invention whereby the microorganisms to be monitored proliferate between the two plates. Panel (A) and (B) illustrate the device at a closed configuration at two different time points after a microorganism-containing sample is loaded in the device, respectively. Top views of the device are shown on the left, and cross-sectional views taken at line bb' or cc' are shown on the right. As depicted, the QMAX device comprises a first plate 10, a second plate 20, and spacers 40. Panel (A) shows the device and the microorganisms shortly after the two plates are brought into the closed configuration, in which the sample is confined by the two plates into a thin layer (the liquidous component of the sample is not shown), and, in this exemplary embodiment, the height of the spacers 40 is selected such that the microorganisms 92 are confined by the two plates into a single layer. Panel (B) shows the device with the microorganisms a certain time period after the two plates entering the closed configuration, when some of the microorganisms have started to divide and generate new individual microorganisms. As an example, the microorganism 92 indicated by the dashed circle in both panels (A) and (B) gives rise to the new individual 94 in panel (B). It is to be noted that, although depicted as static in the figures over time, the microorganisms between the two plates, particularly the live individuals, may displace on their own in spite of the fact that in the thin layer, the fluidic sample is stagnant relative to the plates at the closed configuration.

Figure 4:
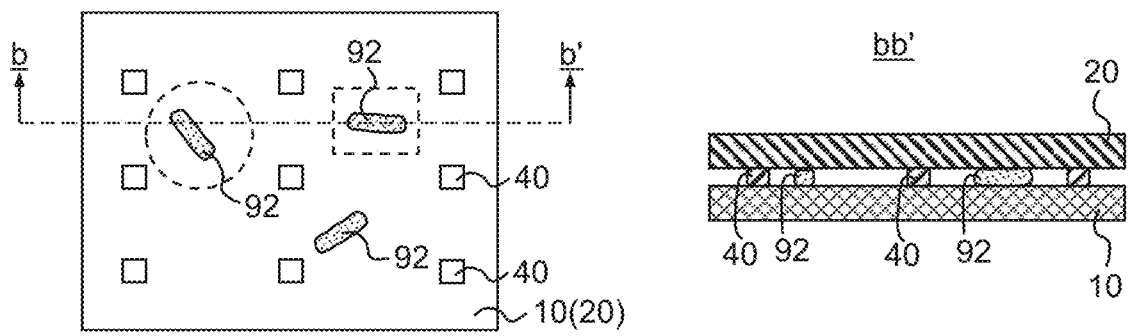
FIG. 4 shows another exemplary embodiment of the present invention whereby the test reagent affects the survival of the microorganisms.
Figure 4:
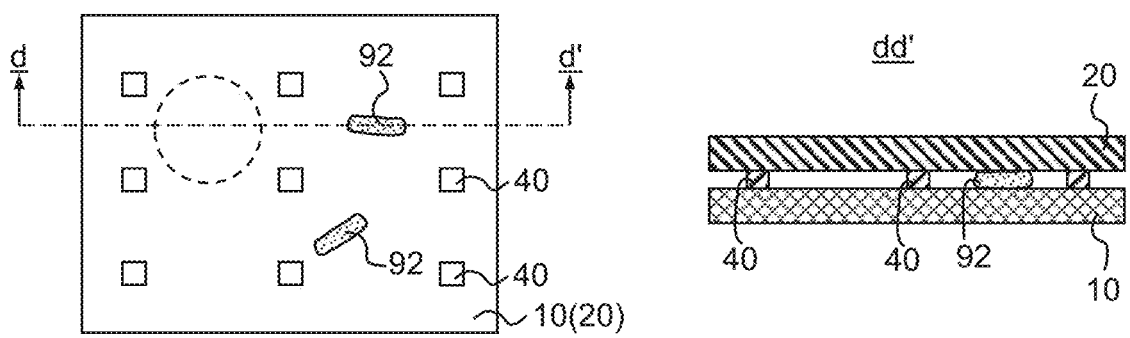
Figure 4:
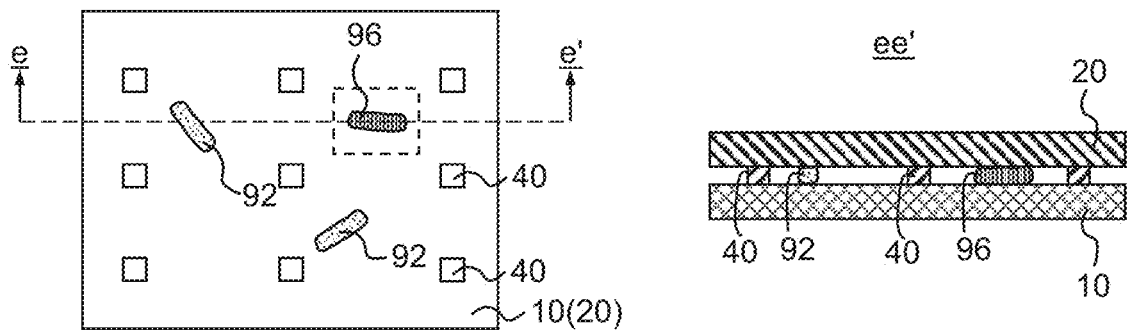

FIG. 4 shows another exemplary embodiment of the present invention whereby the test reagent affects the survival of the microorganisms. Top views of the device are shown on the left, and cross-sectional views taken at line bb', dd' or ee' are shown on the right. Panel (A) depicts the same situation as in FIG. 3 panel (A), while panels (B) and (C) illustrate the potential situations where some of the microorganisms die a certain time period after the two plates enter the closed configuration. In one case, the microorganism individual indicated by the dashed circle in panel (A) die, and its cell integrity is destroyed, seemingly "disappearing" as symbolized by the empty dashed circle in panel (B). In another case, the microorganism individual indicated by the dashed square in panel (A) dies, but it maintains its cell morphology. In this case, a cell viability dye that stains cell corpse indicates the dead individual 96 in the dashed square in panel (C).

In some embodiments, monitoring of cell proliferation is desirable in cases exemplified in FIG. 3, where the proliferation of the microorganisms is suspected as one aspect to be affected by the test reagents. In some embodiments, monitoring of cell number in general is desirable where the changes are suspected to be observed under the influence of the test reagents as to whether and how the microorganisms proliferate (increase in number), and/or die-and-disappear (reduction in number), as exemplified in FIG. 3 and FIG. 4 panel (B), respectively. In some embodiments, monitoring of cell viability is desirable where the changes are suspected to be observed under the influence of the test reagents as to whether and how the microorganisms die but maintain their cell morphology, as exemplified in FIG. 4 panel (C).

Yet, in some embodiments, monitoring of cell morphology is desirable where their morphology is suspected as one aspect to be affected by the test reagents. In some embodiments, monitoring of cell motility is desirable where the cell motility is suspected as one aspect to be affected by the test reagents. In some embodiments, monitoring of some other aspects of the microorganisms are desirable when other needs are to be met.

In some embodiments, monitoring of any combination of the foregoing aspects of the microorganism is possibly desirable.

One important aspect of the present invention is that the QMAX device enables a diverse range of monitoring possibilities to meet different needs, which is addressed in further details below.

Reagents on the Plate(s)

For examining the drug effect on microorganisms, it is normally required to contact the microorganisms with various reagents, including the test reagent(s). In some embodiments, the various reagents are added into the sample containing the microorganisms before the sample is deposited on one or both of the plates. However, it is one aspect of the present invention to provide a QMAX device and method, in which the reagents are coated on one or both of the plates and to be added into the sample upon contacting the sample.

In some embodiments, the sample to be analyzed by the QMAX device is preloaded with the test reagent, and the QMAX device is to be used for monitoring the microorganisms over time alone. In some embodiments, the test reagent is coated on the sample contact area of one or both of the plates, and is configured to, upon contacting the sample, be dissolved into the sample and diffuse in the sample. In some embodiments, the test reagent comprises at least two parts, one of which is preloaded into the sample, while the other of which is coated on the plate(s).

In some embodiments, multiplexed tests are performed with a single QMAX device. In some embodiments, different species of test reagents are coated at different locations in the sample contact area of the plate(s). In some embodiments, test agent of the same species but different concentrations are coated at different locations in the sample contact area of the plate(s). In some embodiments, the different test reagents and/or the same test reagent of different concentrations are coated on the plate with fluid isolation, for instance, there are wall structures on the plate sample contact area to segregate the different sub-regions. In some embodiments, there is no fluidic isolation between the different sub-regions, and the sub-regions are "separated" from one another as a result of the limited lateral diffusion in the thin layer.

In some embodiments, one or both of the plates comprise, on the respective sample contact area, a control zone and an experimental zone, wherein the experimental zone comprises one or more test reagents that, upon contacting the sample, are dissolved and diffuses in the sample, and wherein the control zone comprises no such test reagents. In some embodiments, the control zone and the experimental zone are fluidically isolated. In some embodiments, the control zone and experimental zone are not fluidically isolated, while the microorganisms are not capable of moving across different zones within the time period of the examination. Comparing the microorganisms in the experimental zone versus the control zone facilitate the determination of the effects of the test reagent(s) on the microorganisms.

In some embodiments, the test reagent comprises an antibiotics, such as, but not limited to, Actinomycin D, Actinonin, Aculeacin A, Acycloguanosine, Adenine 913-D-arabinofuranoside, Alamethicin, Alamethicin, L-Alanyl-L-1-aminoethylphosphonic acid, Albendazole, 17-(Allylamino)-17-demethoxygeldanamycin, Amastatin, Amikacin, Amikacin, 7-Aminoactinomycin D, 7-Aminocephalosporanic acid, N-(6-Aminohexyl)-5-chloro-1-naphthalenesulfonamide, (+)-6-Aminopenicillanic acid, Amoxicillin, Amphotericin B, Ampicillin, Anhydroerythromycin A, Anisomycin, Antimycin A, Antimycin A2, Antipain, Aphidicolin, Apicidin, Apoptolidin A, Apramycin, Artesunate, Ascochlorin, Ascomycin, 5-Azacytidine, Azaserine, Azithromycin, Azlocillin, Bacitracin, Bactenecin, Bafilomycin A1, Bafilomycin B1, Bestatin, Beta D-4 human recombinant, Beta D-1 (36 aa) human recombinant, Beta D-1 (47 aa) human recombinant, Bithionol VETRANAL™, Blasticidine S, Bleomycin, BM-Cyclin, Borrelidin, Brefeldin A, Caerulomycin A, Calcium ionophore III Selectophore™, Calcium Ionophore A23187, Calcium Ionophore A23187, Calcium Ionophore A23187, (S)-(+)-Camptothecin, Capreomycin, Carbadox, Carbenicillin, Carboplatin, Cecropin A, Cecropin B, Cecropin P1 Porcine, Cefaclor, Cefalexin VETRANAL™, Cefazoli, Cefixime, Cefmetazole, Cefoperazone, Cefotaxime, Cefsulodin, Ceftazidime, Ceftriaxone, Cephalexin, Cephalomannine, Cephalothin, Cephradine, Cercosporin, Cerulenin, Cetylpyridinium, Chloramphenicol, Chlorhexidine, Chloroquine, Chlortetracycline, Chromomycin A3, Chrysomycin A, Chrysomycin B, Cinnamycin, Cinoxacin, Ciprofloxacin, Clarithromycin, Cleboptide, Clindamycin, Clofazimine, Clotrimazole, Cloxacillin, Colistin, Colominic acid, Compound 48/80, Concanamycin A, Cordycepin, Coumermycin A1, Cryptotanshinone, Crystal Violet, Cycloheximide, D-Cycloserine, Cyclosporin A, Cyclosporin C, Cytochalasin D, Cytochalasin B, Dacarbazine antineoplastic purine analog, Daunorubicin, 10-Deacetylbaccatin III, Decoyinine, Defensin HNP-1, Defensin HNP-2, Demeclocycline, 1-Deoxymannojirimycin, 1-Deoxynojirimycin, cis-Diamineplatinum(II), 6,9-Diamino-2-ethoxyacridine-DL-lactate, cis-Diammineplatinum (II), 6-Diazo-5-oxo-L-norleucine, 5,7-Dichloro-8-hydroxy-2-methylquinoline, Dichlorophene PESTANAL®, Dicloxacillin, Diethylcarbamazine, Diethylcarbamazine, Difloxacin, Dihydrostreptomycin, Dihydrostreptomycin, Diloxanide furoate, Dimetridazole, Dirithromycin, Doxorubicin, Doxycycline, Duramycin, Econazole, Elafin, Embelin, Emetine, Enrofloxacin, Erythromycin, Ethambutol, Etoposide, Fengycin, Filipin, Florfenicol, Flubendazol VETRANAL™, Fluconazole, Flumequine, Flumethasone, 5-Fluorocytosine nucleoside analog, Flurbiprofen cyclooxygenase inhibitor, Formycin A, Fumagillin, Fumitremorgin C, Furazolidone, Fusaric acid, G 418, Ganciclovir, Gatifloxacin, Geldanamycin, Gentamicin, Gentamicin, Gentian Violet, Gliotoxin, Gramicidins, Griseofulvin, Herbimycin A, Hexadecylpyridinium, Honokiol, Hydrocortisone 21, 8-Hydroxyquinoline, 4-Hydroxytamoxifen, (Z)-4-Hydroxytamoxifen, Hygromycin B, Ikarugamycin, Imipenem, Indomethacin, Indomethacin, Ionomycin, Irgasan, Itraconazole, Iturin A, Ivermectin, Josamycin, K-252a, K-252b, Kanamycins, Kasugamycin, Kendomycin, Ketoconazole, Kirromycin, L-(+)-Lactic acid, Lactoferricin B, Leptomycin A, Leptomycin B, Levamisol, Levofloxacin, Lincomycin, Listeria mono Selective Supplement I, LL-37, Lomefloxacin, Lysostaphin, Magainin I, Mebendazole, Meclocycline, Menadione, 2-Mercaptopyridine N-oxide, N-Methyl-1-deoxynojirimycin, 2-Methyl-4-isothiazolin-3-one hydrochloride, Metronidazole, Mevastatin, (±)-Miconazole, Minocycline, Mithramycin A, Mitomycin C, Monensin, Morantel, Moxalactam, Mupirocin, Mycosubtilin, Myxothiazol, Prothionamide, Nafcillin, Naftifine, Nalidixic acid, Narasin, Neocarzinostatin, Neomycin, Netilmicin, Netropsin, Niclosamide, Nigericin, Nikkomycin Z, Ni sin, Nitrofurantoin, Nogalamycin, Nonactin, Norfloxacin, Nourseothricin, Novobiocin, NP-1, Nystatin, Ochratoxin A, Ofloxacin, Oligomycin, Oligomycin A, Oxacillin, Oxantel, Oxolinic acid quinolone, Oxytetracycline, Oxytetra, Paclitaxel, Paromomycin, Patulin, PD 404,182, Pediocin, Pefloxacin, D-Penicillamine, Penicillin G, Penicillin V, Pentamidine, PGLa, 1,10-Phenanthroline, Phenazine, Phenoxymethylpenicillinic acid, Phleomycin, Phosphomycin, Pimaricin, Pipemidic acid, Piperacillin, Pirarubicin, Platensimycin, Polymyxin B, Poly(vinylpyrrolidone)-Iodine complex, Potassium clavulanate: cellulose (1:1), Potassium Sorbate, Praziquantel, Puromycin, Pyrantel, Pyrazinecarboxamide, Pyronaridine, Pyrrolnitrin, Quinine, 8-Quinolinol, Radicicol, Ramoplanin, Rapamycin, Rebeccamycin, Reveromycin A, Ribavirin, Ribostamycin, Ricobendazole, Rifabutin, Rifampicin, Rifamycin SV, Rifapentine, Rifaximin, Ristomycin, Rolitetracycline, Roxithromycin, Salinomycin, Sangivamycin, Sinefungin, Sisomicin, Sorbic acid, Sordarin, Sparfloxacin, Spectinomycin, Spergualin, Spiramycin, Staurosporine, Streptolysin O, Streptomycin, Streptonigrin, Streptozocin, Succinylsulfathiazole, Sulconazole, Sulfabenzamide, Sulfachloropyridazine, Sulfadiazine, Sulfadimethoxine, Sulfadimidine, Sulfadoxin, Sulfaguanidine, Sulfameter, Sulfamethazine, Sulfamonomethoxine, Sulfanilamide, Sulfanitran, Sulfaquinoxaline, Sulfasalazine, Sulfathiazole, Sulochrin, Surfactin, Swainsonine, Syringomycin E, Tamoxifen, Tazobactam, Teicoplanin, Terbinafine, Terconazole, Tetracycline, Tetramisole, Thiabendazole, Thiamphenicol, Thimerosal, Thiolutin, Thiostrepton, Thio-TEPA, Thymol, Tiamulin, Ticarcillin, Tioconazole, Tobramycin, Aminoglycoside antibiotic, Tobramycin, Tolnaftate, Toyocamycin, Triacsin C, Trichlorfon, Trimethoprim, Tubercidin, Tunicamycin, Tunicamycin C2 homolog, Tylosin, Valacyclovir, Valinomycin, Vinblastine, Virginiamycin S1, Virginiamycin M1, and any analogs, salts, and derivatives thereof.

In some embodiments, the test reagent comprises an antifungal reagent, such as, but not limited to, Polyene anti fungals (Amphotericin B, Candicidin, Filipin, Hamycin, Natamycin, Nystatin, Rimocidin), Imidazoles (e.g. Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole), Triazoles (Albaconazole, Efinaconazole, Epoxiconazole, Fluconazole, Isavuconazole, Itraconazole, Posaconazole, Propiconazole, Ravuconazole, Terconazole, Voriconazole), Thiazoles (e.g. Abafungin), Allylamines (e.g. Amorolfin, Butenafine, Naftifine, and Terbinafine), Echinocandins (e.g. Anidulafungin, Caspofungin, Micafungin), Aurones, Benzoic acid, Ciclopirox, Flucytosine and 5-fluorocytosine, Griseofulvin, Haloprogin, Tolnaftate, Undecylenic acid, Crystal violet, Balsam of Peru, and any analogs, salts, and derivatives thereof.

In addition to or instead of the test reagents, in some embodiments, the QMAX device comprises, on one or both of the plates, a variety of other reagents to be added into the sample, such as, but not limited to, staining dyes to label the microorganisms (cell viability dyes as well as many other dyes), life-supportive reagents to facilitate the survival of the microorganisms (e.g. nutrients, oxygen source, pH buffer), proliferative reagents to maintain or facilitate the proliferation of the microorganisms (e.g. hormones, siderophore).

In some embodiments, the cell viability dyes include, but not limited to, Propidium Iodide (PI), 7-AAD (7-Aminoactinomycin D), Trypan blue, Calcein Violet AM, Calcein AM, Fixable Viability Dye (FVD) conjugated with different fluorophores, SYTO9 and other nucleic acid dyes, Resazurin and Formazan (MTT/XTT) and other mitochondrial dyes, and any combination thereof and the like. In some embodiments, the sample comprises bacteria, and it is desirable to determine the bacterial viability in the sample, the device further comprises, on one or both of the plates, a bacterial viability dye, for instance, PI, SYTO9, and the like, to differentially stain the live cells versus dead cells.

In some embodiments, the dyes for a stain are selected from the group consisting of: Acid fuchsin, Alcian blue 8 GX, Alizarin red S, Aniline blue WS, Auramine O, Azocarmine B, Azocarmine G, Azure A, Azure B, Azure C, Basic fuchsine, Bismarck brown Y, Brilliant cresyl blue, Brilliant green, Carmine, Chlorazol black E, Congo red, C.I. Cresyl violet, Crystal violet, Darrow red, Eosin B, Eosin Y, Erythrosin, Ethyl eosin, Ethyl green, Fast green F C F, Fluorescein Isothiocyanate, Giemsa Stain, Hematoxylin, Hematoxylin & Eosin, Indigo carmine, Janus green B, Jenner stain 1899, Light green SF, Malachite green, Martius yellow, Methyl orange, Methyl violet 2B, Methylene blue, Methylene blue, Methylene violet, (Bernthsen), Neutral red, Nigrosin, Nile blue A, Nuclear fast red, Oil Red, Orange G, Orange II, Orcein, Pararosaniline, Phloxin B, Protargol S, Pyronine B, Pyronine, Resazurin, Rose Bengal, Safranine O, Sudan black B, Sudan III, Sudan IV, Tetrachrome stain (MacNeal), Thionine, Toluidine blue, Weigert, Wright stain, and any combination thereof.

In some embodiments, the dye is conjugated with fluorescent molecules (fluorophores), including, but not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, redshifted green fluorescent protein, yellow-shifted green fluorescent protein, 4-acetamido-4'-isothiocyanatostilbene-2,2' disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5',5"-dibromopyrogallol sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; ophthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of 5 sulforhodamine (Texas Red); N,N, N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo) benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; any combination thereof; and the like.

Imaging and Image Processing

In some embodiments, the examination of the drug effects on the microorganisms is realized by: while the two plates are at the closed configuration as discussed above, monitoring the microorganisms in the layer of uniform thickness and determining the effect of the test reagent on the microorganisms.

In some embodiments, the monitoring is realized through optical methods, and one or both of the plates is transparent, enabling the optical inspection and/or imaging of the microorganisms between the two plates.

In some embodiments, microscopy technique is utilized to monitor the microorganisms in the device. In some embodiments, a standard laboratory microscope is used, while in some embodiments, a miniaturized or custom-designed microscope is used.

In some embodiments, the monitoring is realized through imaging. An imager is utilized to acquire images of signals emanating from the microorganisms in the device. In some embodiments, the imager comprises a camera and a light source for imaging the microorganism in the thin layer.

In some embodiments, a series of images are taken of the microorganisms in the device at discrete time points. In some embodiments, a video is taken of the microorganisms in the device over a certain period of time.

In some embodiments, visual inspection of the microorganisms is performed by a professional or non-professional user of the device, with the aid of the microscope, the acquired images, and/or the acquired video of the microorganisms.

In some embodiments, a processor is utilized for processing the acquired images and/or the acquired video of the microorganisms. The processor comprises electronics, signal processors, hardware and software for receiving and processing the images and identifying and analyzing the microorganisms in the images.

In some embodiments, the step of monitoring and determining comprises:
 i. acquiring a series of images of the plates which contains microorganisms in the layer of uniform thickness sample between the plates at discrete time points;
 ii. identifying and/or counting the microorganisms in at least an area of each of the images; and
 iii. evaluating changes of the microorganisms among at least part of the discrete time points.

In some embodiments, the step of monitoring and determining comprises:
 i. acquiring a video comprising s series of images of the plates which contains microorganisms in the layer of uniform thickness at discrete time points over a first time period;
 ii. identifying and tracking at least a portion of the microorganisms in the video; and
 iii. evaluating changes of the tracked microorganisms over at least a portion of the first time period.

In some embodiments, the step of identifying comprises identifying the microorganisms stained by a dye, and wherein the dye comprises a cell viability dye that indicates whether a stained cell is alive or dead.

In some embodiments, the changes of the microorganisms include, but not limited to, changes in the total number of the microorganism individuals, changes in the concentration of the microorganisms, changes in the morphology of the microorganisms, changes in the motility of the microorganisms, changes in the uptake of the staining dye by the microorganisms, and any combination thereof.

In some embodiments, the changes in the number or concentration of the microorganism individuals are evaluated. The processor is configured to count the number of the identified microorganism in the at least an area of each of the images. In some cases, a concentration of the microorganisms is determined. One advantage of the present invention is, in some embodiments, the spacers control the highly uniform thickness of the final sample layer. Therefore, the volume of the sample in at least an area of each of the images is readily calculated by multiplying the area of interest by the final sample thickness, enabling the easy deduction of the concentration of the microorganisms in the area of interest.

In some embodiments, the changes in the number of the microorganism individuals are evaluated through the tracking of at least part of the microorganisms in the acquired video. As tracking individual microorganisms, the processor is also configured to identify the events when the tracked individual(s) experience cell division (giving rise to new individuals and increasing the number), and/or disappear as a result of cell death and cell body disassembly.

In some embodiments, the changes in the morphology of the microorganisms are evaluated by analyzing the geometrical parameters of the images of each microorganism individuals in the acquired images and/or video.

In some embodiments, the changes in the motility of the microorganisms are evaluated by analyzing the parameters of the movement of the tracked microorganism individuals in the acquired video, such as, but not limited to, moving speed, directions, and duration and frequency of immobility.

In some embodiments, the changes in the uptake of the staining dye by the microorganisms are evaluated by assessing the signals emanating from the staining dye within the boundaries of microorganism individuals.

System for Examining Drug Effects on Microorganisms

It is another aspect of the present invention to provide a system for examining drug effects on microorganisms. And in certain embodiments, the system enables remote health monitoring, counseling, etc.

In some embodiments, the system comprises:

(a) a QMAX device;

(b) an imager, comprising a camera and a light source for imaging the microorganism in the layer of uniform thickness; and (c) a processor, comprising electronics, signal processors, hardware and software for receiving and processing the images and identifying and analyzing the microorganisms in the images.

In some embodiments, the imager is configured to acquire a series of images of the microorganism at discrete time points.

In some embodiments, the processor is configured to receive and analyze the series of images, identify and count the microorganism in a first area of each of the images.

In some embodiments, the imager is configured to acquire a video that comprises a series of images of the microorganisms over a certain time period.

In some embodiments, the processor is configured to receive and analyze the video, identify and track at least a portion of the microorganisms in the video, and evaluate changes of the tracked microorganisms over at least a portion of the first time period.

In some embodiments, a mobile communication device is utilized as the imager and optionally the image processor. In some embodiments, the system comprises:

(a) a QMAX device as described in any foregoing or following embodiment;

(b) a mobile communication device comprising:
   i. an imager that comprises one or a plurality of cameras for imaging the microorganisms in the sample;
   ii. a processor that comprises electronics, signal processors, hardware and software for receiving and/or processing the image of the microorganisms and for remote communication; and (c) a light source from either the mobile communication device or an external source, wherein the light source is configured to provide illumination to the sample for imaging with the cameras.

In some embodiments, the system further comprises:

(d) a housing configured to hold the sample and to be mounted to the mobile communication device.

In some embodiments, the housing comprises optics for facilitating the imaging and/or signal processing of the sample by the mobile communication device, and a mount configured to hold the optics on the mobile communication device.

In some embodiments, the mobile communication device is configured to communicate test results to a medical professional, a medical facility or an insurance company.

In some embodiments, the mobile communication device is further configured to communicate information on the subject with the medical professional, medical facility or insurance company. In some embodiments, the mobile communication device is configured to receive a prescription, diagnosis or a recommendation from a medical professional.

In some embodiments, the mobile communication device communicates with the remote location via a wifi or cellular network.

In some embodiments, the mobile communication device is a mobile phone.

Application

The present invention finds use in, among others, many aspects of the clinical/diagnostic settings.

In some embodiments, the present invention finds use in susceptibility tests, where antimicrobial drugs are screened for their effects on potential microbiological pathogens causing an infection in a patient, in order to help a healthcare professional choose a most effective antimicrobial drug or treatment strategy for treating the patent's infection. In some embodiments, the tests are performed to facilitate the identification of the pathogenic microorganisms. In some embodiments, the QMAX devices, systems, and methods are utilized for examining the effects of antimicrobial drugs on the potential microorganisms causing a condition in a patient or other subject. In some embodiments, high-throughput tests of such where a variety of antimicrobial drugs in a variety of concentrations/doses are applied against the potential microbiological pathogens in parallel using a single device or system that is configured with multiplexing functionality as discussed above.

Table 1 is a chart of common pathogenic bacteria. In some embodiments, the present invention finds use in testing drug effects on one or many of the bacteria listed in the chart.

TABLE 1

Common pathogenic bacteria

| Genus | Species |
|---|---|
| Bacillus | Bacillus anthracis |
| | Bacillus cereus |
| Bartonella | Bartonella henselae |
| | Bartonella quintana |
| Bordetella | Bordetella pertussis |
| Borrelia | Borrelia burgdorferi |
| | Borrelia garinii |
| | Borrelia afzelii |
| | Borrelia recurrentis |
| Brucella | Brucella abortus |
| | Brucella canis |
| | Brucella melitensis |
| | Brucella suis |
| Campylobacter | Campylobacter jejuni |
| Chlamydia and Chlamydophila | Chlamydia pneumoniae |
| | Chlamydia trachomatis |
| | Chlamydophila psittaci |
| Clostridium | Clostridium botulinum |
| | Clostridium difficile |
| | Clostridium perfringens |
| | Clostridium tetani |
| Corynebacterium | Corynebacterium diphtheriae |
| Enterococcus | Enterococcus faecalis |
| | Enterococcus faecium |
| Escherichia | Escherichia coli |
| Francisella | Francisella tularensis |
| Haemophilus | Haemophilus influenzae |
| Helicobacter | Helicobacter pylori |
| Legionella | Legionella pneumophila |
| Leptospira | Leptospira interrogans |
| | Leptospira santarosai |
| | Leptospira weilii |
| | Leptospira noguchii |
| Listeria | Listeria monocytogenes |
| Mycobacterium | Mycobacterium leprae |
| | Mycobacterium tuberculosis |
| | Mycobacterium ulcerans |
| Mycoplasma | Mycoplasma pneumoniae |
| Neisseria | Neisseria gonorrhoeae |
| | Neisseria meningitidis |

TABLE 1-continued

Common pathogenic bacteria

| Genus | Species |
| --- | --- |
| Pseudomonas | Pseudomonas aeruginosa |
| Rickettsia | Rickettsia rickettsii |
| Salmonella | Salmonella typhi |
| | Salmonella typhimurium |
| Shigella | Shigella sonnei |
| Staphylococcus | Staphylococcus aureus |
| | Staphylococcus epidermidis |
| | Staphylococcus saprophyticus |
| Streptococcus | Streptococcus agalactiae |
| | Streptococcus pneumoniae |
| | Streptococcus pyogenes |
| Treponema | Treponema pallidum |
| Ureaplasma | Ureaplasma urealyticum |
| Vibrio | Vibrio cholerae |
| Yersinia | Yersinia pestis |
| | Yersinia enterocolitica |
| | Yersinia pseudotuberculosis |

In some embodiments, the present invention finds use in many other tests involving biological and/or clinical samples besides the susceptibility tests. These samples include, but not limited to, cells, tissues, and bodily fluid. Bodily fluids of interest include but are not limited to, amniotic fluid, aqueous humour, vitreous humour, blood (e.g., whole blood, fractionated blood, plasma, serum, etc.), breast milk, cerebrospinal fluid (CSF), cerumen (earwax), chyle, chime, endolymph, perilymph, feces, gastric acid, gastric juice, lymph, mucus (including nasal drainage and phlegm), pericardial fluid, peritoneal fluid, pleural fluid, pus, rheum, saliva, sebum (skin oil), semen, sputum, sweat, synovial fluid, tears, vomit, urine and exhaled condensate. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled condensate.

In some embodiments, the present invention finds use in many other tests involving microorganisms, such as, but not limited to, environmental tests, foodstuff tests, and forensic tests. The environmental sample may be obtained from any suitable source, such as a river, ocean, lake, rain, snow, sewage, sewage processing runoff, agricultural runoff, industrial runoff, tap water or drinking water, etc. The foodstuff sample may be obtained from any suitable source, such as tap water, drinking water, prepared food, processed food or raw food, etc.

In some embodiments, the sample is directly obtained from the source. In some embodiments, the sample is pre-loaded with reagents or pre-processed for various needs before being deposited on the plate(s) of the device. In some embodiments, the sample to be deposited on the device comprises a product from a culture of the specimen that is directly obtained from the source, when an elevated level of the microorganisms to be analyzed is needed.

Control Plate Spacing and Sample Thickness Using Spacers

According to the present invention, the spacing between the two plates and hence the sample thickness are controlled by using the spacers.

Spacer height. In some embodiments, all spacers have the same pre-determined height. In some embodiments, spacers have different pre-determined heights. In some embodiments, spacers can be divided into groups or regions, wherein each group or region has its own spacer height. And in certain embodiments, the predetermined height of the spacers is an average height of the spacers. In some embodiments, the spacers have approximately the same height. In some embodiments, a percentage of number of the spacers have the same height.

The height of the spacers is selected by a desired regulated spacing between the plates and/or a regulated final sample thickness and the residue sample thickness. The spacer height (the predetermined spacer height), the spacing between the plates, and/or sample thickness is 3 nm or less, 10 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, 500 µm or less, 800 µm or less, 1 mm or less, 2 mm or less, 4 mm or less, or in a range between any two of the values.

The spacer height, the spacing between the plates, and/or sample thickness is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment.

In some embodiments, the spacer height is controlled precisely. The relative precision of the spacer (i.e. the ratio of the deviation to the desired spacer height) is 0.001% or less, 0.01% or less, 0.1% or less; 0.5% or less, 1% or less, 2% or less, 5% or less, 8% or less, 10% or less, 15% or less, 20% or less, 30% or less, 40% or less, 50% or less, 60% or less, 70% or less, 80% or less, 90% or less, 99.9% or less, or in a range between any of the values.

In some embodiments, the spacer height, the spacing between the plates, and/or sample thickness is: (i) equal to or slightly larger than the minimum dimension of an analyte, or (ii) equal to or slightly larger than the maximum dimension of an analyte. The "slightly larger" means that it is about 1% to 5% larger and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

For example, the red blood cell has a disk shape with a minim dimension of 2 µm (disk thickness) and a maximum dimension of 11 µm (a disk diameter). In an embodiment of the present invention, the spacers are selected to make the inner surface spacing of the plates in a relevant area to be 2 µm (equal to the minimum dimension) in one embodiment, 2.2 µm in another embodiment, or 3 (50% larger than the minimum dimension) in other embodiment, but less than the maximum dimension of the red blood cell. Such embodiment has certain advantages in blood cell counting. In one embodiment, for red blood cell counting, by making the inner surface spacing at 2 or 3 µm and any number between the two values, an undiluted whole blood sample is confined in the spacing; on average, each red blood cell (RBC) does not overlap with others, allowing an accurate counting of the red blood cells visually. (Too many overlaps between the RBC's can cause serious errors in counting).

In some embodiments, the spacer height, the spacing between the plates, and/or sample thickness is: (i) equal to or smaller than the minimum dimension of an analyte, or (ii) equal to or slightly smaller than the maximum dimension of an analyte. The "slightly smaller" means that it is about 1% to 5% smaller and any number between the two values.

In some embodiments, the spacer height, the spacing between the plates, and/or sample thickness is larger than the minimum dimension of an analyte (e.g. an analyte has an anisotropic shape), but less than the maximum dimension of the analyte.

In the present invention, in some embodiments, the plates and the spacers are used to regulate not only the thickness of a sample, but also the orientation and/or surface density of the analytes/entity in the sample when the plates are at the closed configuration. When the plates are at a closed configuration, a thinner thickness of the sample results in less analytes/entity per surface area (i.e. less surface concentration).

Spacer lateral dimension. For an open-spacer, the lateral dimensions can be characterized by its lateral dimension (sometimes called width) in the x and y-two orthogonal directions. The lateral dimension of a spacer in each direction is the same or different. In some embodiments, the lateral dimension for each direction (x or y) is 1 nm or less, 3 nm or less, 5 nm or less, 7 nm or less, 10 nm or less, 20 nm or less, 30 nm or less, 40 nm or less, 50 nm or less, 100 nm or less, 200 nm or less, 500 nm or less, 800 nm or less, 1000 nm or less, 1 µm or less, 2 µm or less, 3 µm or less, 5 µm or less, 10 µm or less, 20 µm or less, 30 µm or less, 50 µm or less, 100 µm or less, 150 µm or less, 200 µm or less, 300 µm or less, or 500 µm or less, or in a range between any two of the values.

In some embodiments, the ratio of the lateral dimensions of x toy direction is 1, 1.5, 2, 5, 10, 100, 500, 1000, 10,000, or in a range between any two of the value. In some embodiments, a different ratio is used to regulate the sample flow direction; the larger the ratio, the flow is along one direction (larger size direction).

In some embodiments, different lateral dimensions of the spacers in x and y direction are used as (a) using the spacers as scale-markers to indicate the orientation of the plates, (b) using the spacers to create more sample flow in a preferred direction, or both.

In a preferred embodiment, the period, width, and height of the spacers are substantially the same. In some embodiments, all spacers have the same shape and dimensions. In some embodiments, the spacers have different lateral dimensions.

For enclosed-spacers, in some embodiments, the inner lateral shape and size are selected based on the total volume of a sample to be enclosed by the enclosed spacer(s), wherein the volume size has been described in the present disclosure; and in certain embodiments, the outer lateral shape and size are selected based on the needed strength to support the pressure of the liquid against the spacer and the compress pressure that presses the plates.

In certain embodiments, the aspect ratio of the height to the average lateral dimension of the pillar spacer is 100,000, 10,000, 1,000, 100, 10, 1, 0.1, 0.01, 0.001, 0.0001, 0, 00001, or in a range between any two of the values.

Inter-spacer distance. The spacers can be a single spacer or a plurality of spacers on the plate or in a relevant area of the sample. In some embodiments, the spacers on the plates are configured and/or arranged in an array form, and the array is a periodic, non-periodic array or periodic in some locations of the plate while non-periodic in other locations.

In some embodiments, the periodic array of the spacers is arranged as lattices of square, rectangle, triangle, hexagon, polygon, or any combinations of thereof, where a combination means that different locations of a plate has different spacer lattices.

In some embodiments, the inter-spacer distance of a spacer array is periodic (i.e. uniform inter-spacer distance) in at least one direction of the array. In some embodiments, the inter-spacer distance is configured to improve the uniformity between the plate spacing at a closed configuration.

In some embodiments, the distance between neighboring spacers (i.e. the inter-spacer distance) is 1 µm or less, 5 µm or less, 7 µm or less, 10 µm or less, 20 µm or less, 30 µm or less, 40 µm or less, 50 µm or less, 60 µm or less, 70 µm or less, 80 µm or less, 90 µm or less, 100 µm or less, 200 µm or less, 300 µm or less, 400 µm or less, or in a range between any two of the values.

In certain embodiments, the inter-spacer distance is at 400 µm or less, 500 µm or less, 1 mm or less, 2 mm or less, 3 mm or less, 5 mm or less, 7 mm or less, 10 mm or less, or in any range between the values. In certain embodiments, the inter-spacer distance is a 10 mm or less, 20 mm or less, 30 mm or less, 50 mm or less, 70 mm or less, 100 mm or less, or in any range between the values.

The distance between neighboring spacers (i.e. the inter-spacer distance) is selected so that for a given properties of the plates and a sample, at the closed-configuration of the plates, the sample thickness variation between two neighboring spacers is, in some embodiments, at most 0.5%, 1%, 5%, 10%, 20%, 30%, 50%, 80%, or in any range between the values; or in certain embodiments, at most 80%, 100%, 200%, 400%, or in a range between any two of the values.

Clearly, for maintaining a given sample thickness variation between two neighboring spacers, when a more flexible plate is used, a closer inter-spacer distance is needed.

In a preferred embodiment, the spacer is a periodic square array, wherein the spacer is a pillar that has a height of 2 to 4 µm, an average lateral dimension of from 1 to 20 µm, and inter-spacer spacing of 1 µm to 100 µm.

In a preferred embodiment, the spacer is a periodic square array, wherein the spacer is a pillar that has a height of 2 to 4 µm, an average lateral dimension of from 1 to 20 µm, and inter-spacer spacing of 100 µm to 250 µm.

In a preferred embodiment, the spacer is a periodic square array, wherein the spacer is a pillar that has a height of 4 to 50 µm, an average lateral dimension of from 1 to 20 µm, and inter-spacer spacing of 1 µm to 100 µm.

In a preferred embodiment, the spacer is a periodic square array, wherein the spacer is a pillar that has a height of 4 to 50 µm, an average lateral dimension of from 1 to 20 µm, and inter-spacer spacing of 100 µm to 250 µm.

The period of spacer array is between 1 nm to 100 nm in one preferred embodiment, 100 nm to 500 nm in another preferred embodiment, 500 nm to 1000 nm in a separate preferred embodiment, 1 µm (i.e. 1000 nm) to 2 µm in another preferred embodiment, 2 µm to 3 µm in a separate preferred embodiment, 3 µm to 5 µm in another preferred embodiment, 5 µm to 10 µm in a separate preferred embodiment, and 10 µm to 50 µm in another preferred embodiment, 50 µm to 100 µm in a separate preferred embodiment, 100 µm to 175 µm in a separate preferred embodiment, and 175 µm to 300 µm in a separate preferred embodiment.

Spacer density. The spacers are arranged on the respective plates at a surface density of greater than one per µm$^2$, greater than one per 10 µm$^2$, greater than one per 100 µm$^2$, greater than one per 500 µm², greater than one per 1000 µm², greater than one per 5000 µm², greater than one per 0.01 mm², greater than one per 0.1 mm², greater than one per 1 mm², greater than one per 5 mm², greater than one per 10 mm², greater than one per 100 mm², greater than one per 1000 mm², greater than one per 10000 mm², or in a range between any two of the values. In some embodiments, the spacers have a density of at least 1/mm², at least 10/mm², at least 50/mm², at least 100/mm², at least 1,000/mm², or at least 10,000/mm².

Spacer area filling factor is defined as the ratio of spacer area to the total area or the ratio of spacer period to the width. In some embodiments, the filling factor is at least 1%, 2%, 3%, 4%, 5%, 6%, 7%, 8%, 9%, 10%, 20%, or in the range between any of the two values. In certain embodiments, the filling factor is at least 2.3%.

The device that comprises two plates and spacers, wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the fourth power of the inter-spacer-distance (ISD) divided by the thickness (h) and the Young's modulus (E) of the flexible plate (ISD^4/(hE)) is 5×10^5 um3/GPa or less.

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The device that comprises two plates and spacers, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD^4/(hE)) is 5×10^6 um^3/GPa or less.

The device that comprises two plates and spacers, wherein the ratio of the inter-spacing distance of the spacers to the average width of the spacer is 2 or larger, and the filling factor of the spacers multiplied by the Young's modulus of the spacers is 2 MPa or larger.

EXAMPLES OF PRESENT INVENTION

A1. A device for examining drug effects on microorganisms, comprising:
  a first plate, a second plate, and spacers, wherein
  i. the plates are movable relative to each other into different configurations, including an open configuration and a closed configuration;
  ii. each of the plates has, on its respective sample surface, a sample contact area for contacting a sample, wherein the sample comprises a microorganism to be analyzed, and
  iii. one or both of the plates comprise the spacers that are fixed to the respective sample contact area, the spacers have a predetermined highly uniform height, and at least one of the spacers is inside the sample contact area,
  wherein in the open configuration, the two plates are partially or entirely separated apart, the spacing between the plates is not regulated by the spacers, and the sample is deposited on one or both of the plates;
  wherein in the closed configuration, which is configured after deposition of the sample in the open configuration: at least part of the sample is compressed by the two plates into a layer of highly uniform thickness, and the uniform thickness of the layer is confined by the sample contact surfaces of the plates and is regulated by the plates and the spacers.

B0. A system for examining drug effects on microorganisms, comprising:
  (a) a device of any of A embodiments;
  (b) an imager, comprising a camera and a light source for imaging the microorganism in the layer of uniform thickness; and
  (c) a processor, comprising electronics, signal processors, hardware and software for receiving and processing the images and identifying and analyzing the microorganisms in the images.

B1. A system for examining drug effects on microorganisms, comprising:
  (a) a device of any of A embodiments;
  (b) a mobile communication device comprising:
    i. an imager that comprises one or a plurality of cameras for imaging the microorganisms in the sample;
    ii. a processor that comprises electronics, signal processors, hardware and software for receiving and/or processing the image of the microorganisms and for remote communication; and
  (c) a light source from either the mobile communication device or an external source, wherein the light source is configured to provide illumination to the sample for imaging with the cameras.

C1. A method of examining drug effects on microorganisms, comprising the steps of:
  (a) obtaining a sample, which comprises a microorganism to be analyzed and is mixed with a test reagent;
  (b) obtaining a first and second plates that are movable relative to each other into different configurations, including an open configuration and a closed configuration, wherein:
    i. each plate, on its respective surface, has a sample contact area for contacting the sample, and
    ii. one or both of the plates comprise spacers that are fixed with a respective sample contact surface,
      wherein the spacers have a predetermined substantially uniform height, and at least one of the spacers is inside the sample contact area;
  (c) depositing the sample on one or both of the plates when the plates are in an open configuration,
    wherein in the open configuration the two plates are partially or entirely separated apart and the spacing between the plates is not regulated by the spacers;
  (d) after (c), bringing the two plates together and pressing the plates into a closed configuration, wherein in the closed configuration: at least part of the sample is compressed by the two plates into a layer of highly uniform thickness, the uniform thickness of the layer is confined by the sample surfaces of the two plates and is regulated by the spacers and the plates;

(e) while the plates are at the closed configuration, monitoring the microorganisms in the layer of uniform thickness and determining the effect of the test reagent on the microorganisms.

CC1. A method of examining drug effects on microorganisms, comprising the steps of:
   (a) obtaining a sample, which comprises a microorganism to be analyzed;
   (b) obtaining a first and second plates that are movable relative to each other into different configurations, including an open configuration and a closed configuration, wherein:
      i. each plate, on its respective surface, has a sample contact area for contacting the sample,
      ii. one or both of the plates comprise spacers that are fixed with a respective sample contact surface, and
      iii. at least one of the plates comprise a test reagent on the respective sample contact area that, upon contacting the sample, is dissolved and diffuses in the sample,
         wherein the spacers have a predetermined substantially uniform height, and at least one of the spacers is inside the sample contact area;
   (c) depositing the sample on one or both of the plates when the plates are in an open configuration,
      wherein in the open configuration the two plates are partially or entirely separated apart and the spacing between the plates is not regulated by the spacers;
   (d) after (c), bringing the two plates together and pressing the plates into a closed configuration, wherein in the closed configuration: at least part of the sample is compressed by the two plates into a layer of highly uniform thickness, the uniform thickness of the layer is confined by the sample surfaces of the two plates and is regulated by the spacers and the plates;
   (e) while the plates are at the closed configuration, monitoring the microorganisms in the layer of uniform thickness and determining the effect of the test reagent on the microorganisms.

A2. The device, system, or method of any prior embodiments, wherein one or both of the plates comprise, on the respective sample contact area, one or more test reagents that, upon contacting the sample, are dissolved and diffuses in the sample.

A3. The device, system, or method of any prior embodiments, wherein one or both of the plates comprise, on the respective sample contact area, a control zone and an experimental zone, wherein the experimental zone comprises one or more test reagents that, upon contacting the sample, are dissolved and diffuses in the sample, and wherein the control zone comprises no such test reagents.

A4. The device, system, or method of any prior embodiments, wherein the uniform height of the spacers is equal to or less than an average dimension of the microorganisms.

A5. The device, system, or method of any prior embodiments, wherein the uniform height of the spacers is in the range of 75% to 125% of an average dimension of the microorganisms.

A6. The device, system, or method of any prior embodiments, wherein at least one of the plates is transparent.

A7. The device, system, or method of any prior embodiments, wherein one or both of the plates comprise, on the respective sample contact area, a dye that, upon contacting the sample, is dissolved in the sample and stains the microorganisms.

A8. The device, system, or method of embodiment A4, wherein the dye is fluorescently labeled.

A9. The device, system, or method of any prior embodiments, wherein one or both of the plates comprise, on the respective sample contact area, a cell viability dye that is selected from the group consisting of: Propidium Iodide, 7-AAD, Trypan blue, Calcein Violet AM, Calcein AM, Fixable Viability Dyes, SYTO9 and other nucleic acid dyes, Resazurin and Formazan (MTT/XTT) and other mitochondrial dyes, and any combination thereof.

A10. The device, system, or method of any prior embodiments, wherein the sample comprises reagents that facilitate the survival and/or division of the microorganism.

A11. The device, system, or method of any prior embodiments, wherein one or both of the plates comprise, on the respective sample contact area, reagents that facilitate the survival and/or division of the microorganism.

B2. The system of any prior embodiments, further comprising:
   (d) a housing configured to hold the sample and to be mounted to the mobile communication device.

B3. The system of any prior embodiments, wherein the imager is configured to acquire a series of images of the microorganism at discrete time points.

B4. The system of embodiment B3, wherein the processor is configured to receive and analyze the series of images, identify and count the microorganism in a first area of each of the images.

B5. The system of any prior embodiments, wherein the imager is configured to acquire a video that comprises a series of images of the microorganisms over a first time period.

B6. The system of embodiment B5, wherein the processor is configured to receive and analyze the video, identify and track at least a portion of the microorganisms in the video, and evaluate changes of the tracked microorganisms over at least a portion of the first time period.

B7. The system of any prior embodiments, wherein the housing comprises optics for facilitating the imaging and/or signal processing of the sample by the mobile communication device, and a mount configured to hold the optics on the mobile communication device.

B8. The system of any prior embodiments, wherein the mobile communication device is configured to communicate test results to a medical professional, a medical facility or an insurance company.

B9. The system of any prior embodiments, wherein the mobile communication device is further configured to communicate information on the subject with the medical professional, medical facility or insurance company.

B10. The system of any prior embodiments, wherein the mobile communication device is configured to receive a prescription, diagnosis or a recommendation from a medical professional.

B11. The system of any prior embodiments, wherein the mobile communication device communicates with the remote location via a wifi or cellular network.

B12. The system of any prior embodiments, wherein the mobile communication device is a mobile phone.

B13. The system of any prior embodiments, further comprising a temperature control element that maintains the sample deposited between the two plates at a temperature that facilitates the survival and/or division of the microorganisms.

C2. The method of any prior embodiments, wherein the step (e) of monitoring and determining is performed by a mobile communication device that comprises:
   i. an imager that comprises one or a plurality of cameras for imaging the microorganisms in the sample; and
   ii. a processor that comprises electronics, signal processors, hardware and software for receiving and/or processing the image of the microorganisms and for remote communication; and a light source from either the mobile communication device or an external source, wherein the light source is configured to provide illumination to the sample for imaging with the cameras.

C3. The method of any prior embodiments, wherein the step (e) of monitoring and determining comprises:
   i. acquiring a series of images of the platelets in the layer of uniform thickness at discrete time points;
   ii. identifying and counting the microorganisms in at least an area of each of the images; and
   iii. evaluating changes of the microorganisms among at least part of the discrete time points.

C4. The method of any prior embodiments, wherein the step (e) of monitoring and determining comprises:
   i. acquiring a video comprising s series of images of the plates in the layer of uniform thickness over a first time period;
   ii. identifying and tracking at least a portion of the microorganisms in the video; and
   iii. evaluating changes of the tracked microorganisms over at least a portion of the first time period.

C5. The method of any prior embodiment C3 or C4, wherein the step of identifying comprises identifying the microorganisms stained by a dye, and wherein the dye comprises a cell viability dye that indicates whether a stained cell is alive or dead.

C6. The method of embodiment C5, wherein the cell viability dye is selected from the group consisting of: Propidium Iodide, 7-AAD, Trypan blue, Calcein Violet AM, Calcein AM, Fixable Viability Dyes, SYTO9 and other nucleic acid dyes, Resazurin and Formazan (MTT/XTT) and other mitochondrial dyes, and any combination thereof.

C7. The method of any prior embodiments, further comprising:
   maintaining the sample at a temperature that facilitates the survival and/or division of the microorganisms while the plates are at the closed configuration.

E1. The device, system, or method of any prior embodiments, wherein the spacers have:
   i. a shape of pillar with substantially uniform cross-section and a flat top surface;
   ii. a ratio of the width to the height equal or larger than one;
   iii. a filling factor of equal to 1% or larger; and
   iv. a product of the filling factor and the Young's modulus of the spacer is 2 MPa or larger,
   wherein the filling factor is the ratio of the spacer contact area to the total plate area.

E2. The device, system, or method of any prior embodiments, wherein an average value of the uniform thickness of the layer is substantially the same as the uniform height of the spacer with a variation of less than 10%.

E3. The device, system, or method of any prior embodiments, wherein the variation of the layer of uniform thickness is less than 30 nm.

E4. The device, system, or method of any prior embodiments, wherein the layer of uniform thickness sample has a thickness uniformity of up to +/−5%.

E5. The device, system, or method of any prior embodiments, wherein the spacers are pillars with a cross-sectional shape selected from round, polygonal, circular, square, rectangular, oval, elliptical, or any combination of the same.

E6. The device, system, or method of any prior embodiments, wherein the spacers have:
   i. a shape of pillar with substantially uniform cross-section and a flat top surface;
   ii. a ratio of the width to the height equal or larger than one;
   iii. a predetermined constant inter-spacer distance that is in the range of 10 $\mu$m to 200 $\mu$m;
   iv. a filling factor of equal to 1% or larger; and
   v. a product of the filling factor and the Young's modulus of the spacer is 2 MPa or larger.
   wherein the filling factor is the ratio of the spacer contact area to a total plate area.

E7. The device, system, or method of any prior embodiments, wherein pressing the plates into the closed configuration is conducted either in parallel or sequentially, the parallel pressing applies an external force on an intended area at the same time, and the sequential pressing applies an external force on a part of an intended area and gradually move to other area.

E8. The device, system, or method of any prior embodiments, wherein the layer of uniform thickness sample has a thickness uniformity of up to +/−5%.

Related Documents

The present invention includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

(1) Definitions

The terms used in describing the devices, systems, and methods herein disclosed are defined in the current application, or in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated in reference by their entireties.

(2) Spacer ad Uniformity

The devices, systems, and methods herein disclosed can include or use QMAX cards for sample detection, analysis, and quantification. In some embodiments, the QMAX card comprises spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

(3) Hinges, Notches, Recesses and Sliders

The devices, systems, and methods herein disclosed can include or use QMAX cards for sample detection, analysis, and quantification. In some embodiments, the QMAX card comprises hinges, notches, recesses, and sliders, which help to facilitate the manipulation of the QMAX card and the measurement of the samples. The structure, material, function, variation and dimension of the hinges, notches, recesses, and sliders are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

(4) Card, Sliders, and Smartphone Detection System

The devices, systems, and methods herein disclosed can include or use QMAX cards for sample detection, analysis, and quantification. In some embodiments, the QMAX cards are used together with sliders that allow the card to be read by a smartphone detection system. The structure, material, function, variation, dimension and connection of the QMAX card, the sliders, and the smartphone detection system are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

(5) Detection Methods

The devices, systems, and methods herein disclosed can include or be used in various types of detection methods. The detection methods are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

(6) Labels

The devices, systems, and methods herein disclosed can employ various types of labels. The labels are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

(7) Biomarkers

The devices, systems, and methods herein disclosed can employ various types of biomarkers. The biomarkers are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

(8) Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

(9) Applications (Field and Samples)

The devices, systems, and methods herein disclosed can be used for various applications (fields and samples). The applications are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, and U.S. Provisional Application No. 62/456,065, which was filed on Feb. 7, 2017, and are all hereby incorporated by reference in their entireties.

Additional Notes

Further examples of inventive subject matter according to the present disclosure are described in the following enumerated paragraphs.

It must be noted that as used herein and in the appended claims, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used here, the term "analyte" refers to a molecule (e.g., a protein, peptides, DNA, RNA, nucleic acid, or other molecule) or molecules, cells, tissues, viruses, and nanoparticles with different shapes. It can also be referred to as any substance that is suitable for testing in the present invention.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Where numerical ranges are mentioned herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

1. Samples

The devices, apparatus, systems, and methods herein disclosed can be used for samples such as but not limited to diagnostic samples, clinical samples, environmental samples and foodstuff samples. The types of sample include but are not limited to the samples listed, described and/or summarized in PCT Application (designating U.S.) Nos. PCT/US2016/045437 and PCT/US0216/051775, which were respectively filed on Aug. 10, 2016 and Sep. 14, 2016, and are hereby incorporated by reference by their entireties.

For example, in some embodiments, the devices, apparatus, systems, and methods herein disclosed are used for a sample that includes cells, tissues, bodily fluids and/or a mixture thereof. In some embodiments, the sample comprises a human body fluid. In some embodiments, the sample comprises at least one of cells, tissues, bodily fluids, stool, amniotic fluid, aqueous humour, vitreous humour, blood, whole blood, fractionated blood, plasma, serum, breast milk, cerebrospinal fluid, cerumen, chyle, chime, endolymph, perilymph, feces, gastric acid, gastric juice, lymph, mucus, nasal drainage, phlegm, pericardial fluid, peritoneal fluid, pleural fluid, pus, rheum, saliva, sebum, semen, sputum, sweat, synovial fluid, tears, vomit, urine, and exhaled breath condensate.

In some embodiments, the devices, apparatus, systems, and methods herein disclosed are used for an environmental sample that is obtained from any suitable source, such as but not limited to: river, lake, pond, ocean, glaciers, icebergs, rain, snow, sewage, reservoirs, tap water, drinking water, etc.; solid samples from soil, compost, sand, rocks, concrete, wood, brick, sewage, etc.; and gaseous samples from the air, underwater heat vents, industrial exhaust, vehicular exhaust, etc. In certain embodiments, the environmental sample is fresh from the source; in certain embodiments, the environmental sample is processed. For example, samples that are not in liquid form are converted to liquid form before the subject devices, apparatus, systems, and methods are applied.

In some embodiments, the devices, apparatus, systems, and methods herein disclosed are used for a foodstuff sample, which is suitable or has the potential to become suitable for animal consumption, e.g., human consumption. In some embodiments, a foodstuff sample includes raw ingredients, cooked or processed food, plant and animal sources of food, preprocessed food as well as partially or fully processed food, etc. In certain embodiments, samples that are not in liquid form are converted to liquid form before the subject devices, apparatus, systems, and methods are applied.

The subject devices, apparatus, systems, and methods can be used to analyze any volume of the sample. Examples of the volumes include, but are not limited to, about 10 mL or less, 5 mL or less, 3 mL or less, 1 microliter ($\mu L$, also "uL" herein) or less, 500 $\mu L$ or less, 300 $\mu L$ or less, 250 $\mu L$ or less, 200 $\mu L$ or less, 170 $\mu L$ or less, 150 $\mu L$ or less, 125 $\mu L$ or less, 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 pL or less, 1 pL or less, or a range between any two of the values.

In some embodiments, the volume of the sample includes, but is not limited to, about 100 $\mu L$ or less, 75 $\mu L$ or less, 50 $\mu L$ or less, 25 $\mu L$ or less, 20 $\mu L$ or less, 15 $\mu L$ or less, 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 pL or less, 1 pL or less, or a range between any two of the values. In some embodiments, the volume of the sample includes, but is not limited to about 10 $\mu L$ or less, 5 $\mu L$ or less, 3 $\mu L$ or less, 1 $\mu L$ or less, 0.5 $\mu L$ or less, 0.1 $\mu L$ or less, 0.05 $\mu L$ or less, 0.001 $\mu L$ or less, 0.0005 $\mu L$ or less, 0.0001 $\mu L$ or less, 10 pL or less, 1 pL or less, or a range between any two of the values.

In some embodiments, the amount of the sample is about a drop of liquid. In certain embodiments, the amount of sample is the amount collected from a pricked finger or fingerstick. In certain embodiments, the amount of sample is the amount collected from a microneedle, micropipette or a venous draw.

In certain embodiments, the sample holder is configured to hold a fluidic sample. In certain embodiments, the sample holder is configured to compress at least part of the fluidic sample into a thin layer. In certain embodiments, the sample holder comprises structures that are configured to heat and/or cool the sample. In certain embodiments, the heating source provides electromagnetic waves that can be absorbed by certain structures in the sample holder to change the temperature of the sample. In certain embodiments, the signal sensor is configured to detect and/or measure a signal from the sample. In certain embodiments, the signal sensor is configured to detect and/or measure an analyte in the sample. In certain embodiments, the heat sink is configured to absorb heat from the sample holder and/or the heating source. In certain embodiments, the heat sink comprises a chamber that at least partly enclose the sample holder.

2. Applications

The devices, apparatus, systems, and methods herein disclosed can be used in various types of biological/chemical sampling, sensing, assays and applications, which include the applications listed, described and/or summarized in PCT Application (designating U.S.) No. PCT/US2016/045437, which was filed on Aug. 10, 2016, and is hereby incorporated by reference by its entirety.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

3. Analytes, Biomarkers, and Diseases

The devices, apparatus, systems, and methods herein disclosed can be used for the detection, purification and/or quantification of various analytes. In some embodiments, the analytes are biomarkers that associated with various diseases. In some embodiments, the analytes and/or biomarkers are indicative of the presence, severity, and/or stage of the diseases. The analytes, biomarkers, and/or diseases that can be detected and/or measured with the devices, apparatus, systems, and/or method of the present invention include the analytes, biomarkers, and/or diseases listed, described and/or summarized in PCT Application (designating U.S.) Nos. PCT/US2016/045437 filed on Aug. 10, 2016, and PCT Application No. PCT/US2016/054025 filed on Sep. 27, 2016, and U.S. Provisional Application Nos. 62/234,538 filed on Sep. 29, 2015, 62/233,885 filed on Sep. 28, 2015, 62/293,188 filed on Feb. 9, 2016, and 62/305,123 filed on Mar. 8, 2016, which are all hereby incorporated by reference by their entireties. For example, the devices, apparatus, systems, and methods herein disclosed can be used in (a) the detection, purification and quantification of chemical compounds or biomolecules that correlates with the stage of certain diseases, e.g., infectious and parasitic disease, injuries, cardiovascular disease, cancer, mental disorders, neuropsychiatric disorders and organic diseases, e.g., pulmonary diseases, renal diseases, (b) the detection, purification and quantification of microorganism, e.g., virus, fungus and bacteria from environment, e.g., water, soil, or biological samples, e.g., tissues, bodily fluids, (c) the detection, quantification of chemical compounds or biological samples that pose hazard to food safety or national security, e.g. toxic waste, anthrax, (d) quantification of vital parameters in medical or physiological monitor, e.g., glucose, blood oxygen level, total blood count, (e) the detection and quantification of specific DNA or RNA from biosamples, e.g., cells, viruses, bodily fluids, (f) the sequencing and comparing of genetic sequences in DNA in the chromosomes and mitochondria for genome analysis or (g) to detect reaction products, e.g., during synthesis or purification of pharmaceuticals.

In some embodiments, the analyte can be a biomarker, an environmental marker, or a foodstuff marker. The sample in some instances is a liquid sample, and can be a diagnostic sample (such as saliva, serum, blood, sputum, urine, sweat, lacrima, semen, or mucus); an environmental sample obtained from a river, ocean, lake, rain, snow, sewage, sewage processing runoff, agricultural runoff, industrial runoff, tap water or drinking water; or a foodstuff sample obtained from tap water, drinking water, prepared food, processed food or raw food.

In any embodiment, the sample can be a diagnostic sample obtained from a subject, the analyte can be a biomarker, and the measured the amount of the analyte in the sample can be diagnostic of a disease or a condition.

In any embodiment, the devices, apparatus, systems, and methods in the present invention can further include diagnosing the subject based on information including the measured amount of the biomarker in the sample. In some cases, the diagnosing step includes sending data containing the measured amount of the biomarker to a remote location and receiving a diagnosis based on information including the measurement from the remote location.

In any embodiment, the biomarker can be selected from Tables B1, 2, 3 or 7 as disclosed in U.S. Provisional Application Nos. 62/234,538, 62/293,188, and/or 62/305,123, and/or PCT Application No. PCT/US2016/054,025, which are all incorporated in their entireties for all purposes. In some instances, the biomarker is a protein selected from Tables B1, 2, or 3. In some instances, the biomarker is a nucleic acid selected from Tables B2, 3 or 7. In some instances, the biomarker is an infectious agent-derived biomarker selected from Table B2. In some instances, the biomarker is a microRNA (miRNA) selected from Table B7.

In any embodiment, the applying step b) can include isolating miRNA from the sample to generate an isolated miRNA sample, and applying the isolated miRNA sample to the disk-coupled dots-on-pillar antenna (QMAX device) array.

In any embodiment, the QMAX device can contain a plurality of capture agents that each bind to a biomarker selected from Tables B 1, B2, B3 and/or B7, wherein the reading step d) includes obtaining a measure of the amount of the plurality of biomarkers in the sample, and wherein the amount of the plurality of biomarkers in the sample is diagnostic of a disease or condition.

In any embodiment, the capture agent can be an antibody epitope and the biomarker can be an antibody that binds to the antibody epitope. In some embodiments, the antibody epitope includes a biomolecule, or a fragment thereof, selected from Tables B4, B5 or B6. In some embodiments, the antibody epitope includes an allergen, or a fragment thereof, selected from Table B5. In some embodiments, the antibody epitope includes an infectious agent-derived biomolecule, or a fragment thereof, selected from Table B6.

In any embodiment, the QMAX device can contain a plurality of antibody epitopes selected from Tables B4, B5 and/or B6, wherein the reading step d) includes obtaining a measure of the amount of a plurality of epitope-binding antibodies in the sample, and wherein the amount of the plurality of epitope-binding antibodies in the sample is diagnostic of a disease or condition.

In any embodiment, the sample can be an environmental sample, and wherein the analyte can be an environmental marker. In some embodiments, the environmental marker is selected from Table B8 in U.S. Provisional Application No. 62/234,538 and/or PCT Application No. PCT/US2016/054025.

In any embodiment, the method can include receiving or providing a report that indicates the safety or harmfulness for a subject to be exposed to the environment from which the sample was obtained.

In any embodiment, the method can include sending data containing the measured amount of the environmental marker to a remote location and receiving a report that indicates the safety or harmfulness for a subject to be exposed to the environment from which the sample was obtained.

In any embodiment, the QMAX device array can include a plurality of capture agents that each binds to an environmental marker selected from Table B8, and wherein the reading step d) can include obtaining a measure of the amount of the plurality of environmental markers in the sample.

In any embodiment, the sample can be a foodstuff sample, wherein the analyte can be a foodstuff marker, and wherein the amount of the foodstuff marker in the sample can correlate with safety of the foodstuff for consumption. In some embodiments, the foodstuff marker is selected from Table B9.

In any embodiment, the method can include receiving or providing a report that indicates the safety or harmfulness for a subject to consume the foodstuff from which the sample is obtained.

In any embodiment, the method can include sending data containing the measured amount of the foodstuff marker to a remote location and receiving a report that indicates the safety or harmfulness for a subject to consume the foodstuff from which the sample is obtained.

In any embodiment, the devices, apparatus, systems, and methods herein disclosed can include a plurality of capture agents that each binds to a foodstuff marker selected from Table B9 from in U.S. Provisional Application No. 62/234,538 and PCT Application No. PCT/US2016/054025, wherein the obtaining can include obtaining a measure of the amount of the plurality of foodstuff markers in the sample, and wherein the amount of the plurality of foodstuff marker in the sample can correlate with safety of the foodstuff for consumption.

Also provided herein are kits that find use in practicing the devices, systems and methods in the present invention.

The amount of sample can be about a drop of a sample. The amount of sample can be the amount collected from a pricked finger or fingerstick. The amount of sample can be the amount collected from a microneedle or a venous draw.

A sample can be used without further processing after obtaining it from the source, or can be processed, e.g., to enrich for an analyte of interest, remove large particulate matter, dissolve or resuspend a solid sample, etc.

Any suitable method of applying a sample to the QMAX device can be employed. Suitable methods can include using a pipette, dropper, syringe, etc. In certain embodiments, when the QMAX device is located on a support in a dipstick format, as described below, the sample can be applied to the QMAX device by dipping a sample-receiving area of the dipstick into the sample.

A sample can be collected at one time, or at a plurality of times. Samples collected over time can be aggregated and/or processed (by applying to a QMAX device and obtaining a measurement of the amount of analyte in the sample, as described herein) individually. In some instances, measurements obtained over time can be aggregated and can be useful for longitudinal analysis over time to facilitate screening, diagnosis, treatment, and/or disease prevention.

Washing the QMAX device to remove unbound sample components can be done in any convenient manner, as described above. In certain embodiments, the surface of the QMAX device is washed using binding buffer to remove unbound sample components.

Detectable labeling of the analyte can be done by any convenient method. The analyte can be labeled directly or indirectly. In direct labeling, the analyte in the sample is labeled before the sample is applied to the QMAX device. In indirect labeling, an unlabeled analyte in a sample is labeled after the sample is applied to the QMAX device to capture the unlabeled analyte, as described below.

4. Labels

The devices, apparatus, systems, and methods herein disclosed can be used with various types of labels, which include the labels disclosed, described and/or summarized in PCT Application (designating U.S.) No. PCT/US2016/045437, which was filed on Aug. 10, 2016, and is hereby incorporated by reference by its entirety.

In some embodiments, the label is optically detectable, such as but not limited to a fluorescence label. In some embodiments, the labels include, but are not limited to, IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyan-shifted green fluorescent protein, red-shifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol-sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM),5-(4,6-dichlorotriazin-2-yl)amino-fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes; combinations thereof, and the like. Suitable fluorescent proteins and chromogenic proteins include, but are not limited to, a green fluorescent protein (GFP), including, but not limited to, a GFP derived from *Aequoria victoria* or a derivative thereof, e.g., a "humanized" derivative such as Enhanced GFP; a GFP from another species such as *Renilla reniformis, Renilla mulleri*, or *Ptilosarcus guernyi*; "humanized" recombinant GFP (hrGFP); any of a variety of fluorescent and colored proteins from *Anthozoan* species; combinations thereof; and the like.

5. QMAX Device

The devices, apparatus, systems, and methods herein disclosed can include or use a QMAX device ((Q: quantification; M: magnifying; A: adding reagents; X: acceleration; also known as Q-card in some embodiments or compressed regulated open flow (CROF) device), which include the QMAX device listed, described and/or summarized in PCT Application (designating U.S.) Nos. PCT/US2016/045437 filed on Aug. 10, 2016, and U.S. Provisional Application Nos. 62/431,639 filed on Dec. 9, 2016 and 62/456,287 filed on Feb. 8, 2017, which are all hereby incorporated by reference by their entireties.

As used here, the terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not comprise spacers; and the terms refer to a device that comprises a first plate and a second plate that are movable relative to each other into different configurations (including an open configuration and a closed configuration), and that comprises spacers (except some embodiments of the COF) that regulate the spacing between the plates. The term "X-plate" refers to one of the two plates in a CROF card, wherein the spacers are fixed to this plate. More descriptions of the COF Card, CROF Card, and X-plate are described in the provisional application Ser. No. 62/456,065, filed on Feb. 7, 2017, which is incorporated herein in its entirety for all purposes.

The term "compressed open flow (COF)" refers to a method that changes the shape of a flowable sample deposited on a plate by (i) placing other plate on top of at least a part of the sample and (ii) then compressing the sample between the two plates by pushing the two plates towards each other; wherein the compression reduces a thickness of at least a part of the sample and makes the sample flow into open spaces between the plates. The term "compressed regulated open flow" or "CROF" (or "self-calibrated compressed open flow" or "SCOF" or "SCCOF") (also known as QMAX) refers to a particular type of COF, wherein the final thickness of a part or entire sample after the compression is "regulated" by spacers, wherein the spacers are placed between the two plates. Here the CROF device is used interchangeably with the QMAX card.

The term "open configuration" of the two plates in a QMAX process means a configuration in which the two plates are either partially or completely separated apart and the spacing between the plates is not regulated by the spacers The term "closed configuration" of the two plates in a QMAX process means a configuration in which the plates are facing each other, the spacers and a relevant volume of the sample are between the plates, the relevant spacing between the plates, and thus the thickness of the relevant volume of the sample, is regulated by the plates and the spacers, wherein the relevant volume is at least a portion of an entire volume of the sample.

The term "a sample thickness is regulated by the plate and the spacers" in a QMAX process means that for a give condition of the plates, the sample, the spacer, and the plate compressing method, the thickness of at least a port of the sample at the closed configuration of the plates can be predetermined from the properties of the spacers and the plate.

The term "inner surface" or "sample surface" of a plate in a QMAX card refers to the surface of the plate that touches the sample, while the other surface (that does not touch the sample) of the plate is termed "outer surface".

The term "height" or "thickness" of an object in a QMAX process refers to, unless specifically stated, the dimension of the object that is in the direction normal to a surface of the plate. For example, spacer height is the dimension of the spacer in the direction normal to a surface of the plate, and the spacer height and the spacer thickness means the same thing.

The term "area" of an object in a QMAX process refers to, unless specifically stated, the area of the object that is parallel to a surface of the plate. For example, spacer area is the area of the spacer that is parallel to a surface of the plate.

The term of QMAX card refers the device that perform a QMAX (e.g. CROF) process on a sample, and have or not have a hinge that connect the two plates.

The term "QMAX card with a hinge and "QMAX card" are interchangeable.

The term "angle self-maintain", "angle self-maintaining", or "rotation angle self-maintaining" refers to the property of the hinge, which substantially maintains an angle between the two plates, after an external force that moves the plates from an initial angle into the angle is removed from the plates.

In using QMAX card, the two plates need to be open first for sample deposition. However, in some embodiments, the QMAX card from a package has the two plates are in contact each other (e.g. a close position), and to separate them is challenges, since one or both plates are very thing. To facilitate an opening of the QMAX card, opening notch or notches are created at the edges or corners of the first plate or both places, and, at the close position of the plates, a part of the second plate placed over the opening notch, hence in the notch of the first plate, the second plate can be lifted open without a blocking of the first plate.

In the QMAX assay platform, a QMAX card uses two plates to manipulate the shape of a sample into a thin layer (e.g. by compressing). In certain embodiments, the plate manipulation needs to change the relative position (termed: plate configuration) of the two plates several times by human hands or other external forces. There is a need to design the QMAX card to make the hand operation easy and fast.

In QMAX assays, one of the plate configurations is an open configuration, wherein the two plates are completely or partially separated (the spacing between the plates is not controlled by spacers) and a sample can be deposited. Another configuration is a closed configuration, wherein at least part of the sample deposited in the open configuration is compressed by the two plates into a layer of highly uniform thickness, the uniform thickness of the layer is confined by the inner surfaces of the plates and is regulated by the plates and the spacers. In some embodiments, the average spacing between the two plates is more than 300 um.

In a QMAX assay operation, an operator needs to first make the two plates to be in an open configuration ready for sample deposition, then deposit a sample on one or both of the plates, and finally close the plates into a close position. In certain embodiments, the two plates of a QMAX card are initially on top of each other and need to be separated to get into an open configuration for sample deposition. When one of the plate is a thin plastic film (175 um thick PMA), such separation can be difficult to perform by hand. The present invention intends to provide the devices and methods that make the operation of certain assays, such as the QMAX card assay, easy and fast.

In some embodiments, the QMAX device comprises a hinge that connect two or more plates together, so that the plates can open and close in a similar fashion as a book. In some embodiments, the material of the hinge is such that the hinge can self-maintain the angle between the plates after adjustment. In some embodiments, the hinge is configured to maintain the QMAX card in the closed configuration, such that the entire QMAX card can be slide in and slide out a card slot without causing accidental separation of the two plates. In some embodiments, the QMAX device comprises one or more hinges that can control the rotation of more than two plates.

In some embodiments, the hinge is made from a metallic material that is selected from a group consisting of gold, silver, copper, aluminum, iron, tin, platinum, nickel, cobalt, alloys, or any combination of thereof. In some embodiments, the hinge comprises a single layer, which is made from a polymer material, such as but not limited to plastics. The polymer material is selected from the group consisting of acrylate polymers, vinyl polymers, olefin polymers, cellulosic polymers, noncellulosic polymers, polyester polymers, Nylon, cyclic olefin copolymer (COC), poly(methyl methacrylate) (PMMB), polycarbonate (PC), cyclic olefin polymer (COP), liquid crystalline polymer (LCP), polyamide (PB), polyethylene (PE), polyimide (PI), polypropylene (PP), poly(phenylene ether) (PPE), polystyrene (PS), polyoxymethylene (POM), polyether ether ketone (PEEK), polyether sulfone (PES), poly(ethylene phthalate) (PET), polytetrafluoroethylene (PTFE), polyvinyl chloride (PVC), polyvinylidene fluoride (PVDF), polybutylene terephthalate (PBT), fluorinated ethylene propylene (FEP), perfluoroalkoxyalkane (PFB), polydimethylsiloxane (PDMS), rubbers, or any combinations of thereof. In some embodiments, the polymer material is selected from polystyrene, PMMB, PC, COC, COP, other plastic, or any combination of thereof.

In some embodiments, the QMAX device comprises opening mechanisms such as but not limited to notches on plate edges or strips attached to the plates, making is easier for a user to manipulate the positioning of the plates, such as but not limited to separating the plates of by hand.

In some embodiments, the QMAX device comprises trenches on one or both of the plates. In certain embodiments, the trenches limit the flow of the sample on the plate.

6. Spacers

The devices, apparatus, systems, and methods herein disclosed can include or use a device (e.g. a QMAX device), which comprises spacers that are listed, described and/or summarized in PCT Application (designating U.S.) No. PCT/US2016/045437 filed on Aug. 10, 2016, and U. S Provisional Application Nos. 62/431,639 filed on Dec. 9, 2016 and 62/456,287 filed on Feb. 8, 2017, which are all hereby incorporated by reference by their entireties.

In essence, the term "spacers" or "stoppers" refers to, unless stated otherwise, the mechanical objects that set, when being placed between two plates, a limit on the minimum spacing between the two plates that can be reached when compressing the two plates together. Namely, in the compressing, the spacers will stop the relative movement of the two plates to prevent the plate spacing becoming less than a preset (i.e. predetermined) value.

The term "a spacer has a predetermined height" and "spacers have a predetermined inter-spacer distance" means, respectively, that the value of the spacer height and the inter spacer distance is known prior to a QMAX process. It is not predetermined, if the value of the spacer height and the inter-spacer distance is not known prior to a QMAX process. For example, in the case that beads are sprayed on a plate as spacers, where beads are landed at random locations of the plate, the inter-spacer distance is not predetermined. Another example of not predetermined inter spacer distance is that the spacers moves during a QMAX processes.

The term "a spacer is fixed on its respective plate" in a QMAX process means that the spacer is attached to a location of a plate and the attachment to that location is maintained during a QMAX (i.e. the location of the spacer on respective plate does not change) process. An example of "a spacer is fixed with its respective plate" is that a spacer is monolithically made of one piece of material of the plate, and the location of the spacer relative to the plate surface does not change during the QMAX process. An example of "a spacer is not fixed with its respective plate" is that a spacer is glued to a plate by an adhesive, but during a use of the plate, during the QMAX process, the adhesive cannot hold the spacer at its original location on the plate surface and the spacer moves away from its original location on the plate surface.

7. Adaptor

The devices, apparatus, systems, and methods herein disclosed can be used with an adaptor, which is configured to accommodate the device and connect the device to a reader, such as but not limited to a smartphone. In some embodiments, the Q-cards are used together with sliders that allow the card to be inserted into the adaptor so that the card can be read by a smartphone detection system. The structure, material, function, variation, dimension and connection of the Q-card, the sliders, and the adaptor are disclosed, listed, described, and/or summarized in PCT Application (designating U.S.) Nos. PCT/US2016/045437 filed on Aug. 10, 2016 and PCT/US0216/051775 filed on Sep. 14, 2016, US Provisional Application Nos. 62/456,590 filed on Feb. 8, 2017, 62/459,554 filed on Feb. 15, 2017, and 62/460,075 filed on Feb. 8, 2017, all of which applications are incorporated herein in their entireties for all purposes.

In some embodiments, the adaptor comprises a receptacle slot, which is configured to accommodate the QMAX device when the device is in a closed configuration. In certain embodiments, the QMAX device has a sample deposited therein and the adaptor can be connected to a mobile device (e.g. a smartphone) so that the sample can be read by the mobile device. In certain embodiments, the mobile device can detect and/or analyze a signal from the sample. In certain embodiments, the mobile device can capture images of the sample when the sample is in the QMAX device and positioned in the field of view (FOV) of a camera, which in certain embodiments, is part of the mobile device.

In some embodiments, the adaptor comprises optical components, which are configured to enhance, magnify, and/or optimize the production of the signal from the sample. In some embodiments, the optical components include parts that are configured to enhance, magnify, and/or optimize illumination provided to the sample. In certain embodiments, the illumination is provided by a light source that is part of the mobile device. In some embodiments, the optical components include parts that are configured to enhance, magnify, and/or optimize a signal from the sample. The structures, functions, and configurations of the optical components in some embodiments can be found in PCT Application (designating U.S.) Nos. PCT/US2016/045437 filed on Aug. 10, 2016 and PCT/US0216/051775 filed on Sep. 14, 2016, US Provisional Application Nos. 62/456,590 filed on Feb. 8, 2017, 62/459,554 filed on Feb. 15, 2017, and 62/460,075 filed on Feb. 8, 2017, all of which applications are incorporated herein in their entireties for all purposes.

8. Dimensions

The devices, apparatus, systems, and methods herein disclosed can include or use a QMAX device, which can comprise plates and spacers. In some embodiments, the dimension of the individual components of the QMAX device and its adaptor are listed, described and/or summarized in PCT Application (designating U.S.) No. PCT/US2016/045437 filed on Aug. 10, 2016, and U. S Provisional Application Nos. 62/431,639 filed on Dec. 9, 2016 and 62/456,287 filed on Feb. 8, 2017, which are all hereby incorporated by reference by their entireties.

In some embodiments, the dimensions are listed in the Tables below:

Plates:

| Parameters | Embodiments | Preferred Embodiments |
|---|---|---|
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 um or less, 200 um or less, 500 um or less, 1 mm or less, 2 mm or less, 5 mm or less, 10 mm or less, 50 mm or less, or in a range between any two of the values. |
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 mm$^2$; or around 750 mm$^2$. |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 um or less, 10 um or less, 20 um or less, 30 um or less, 40 um or less, 50 um or less, 100 um or less, 200 um or less, 300 um or less, 400 um or less, 500 um or less, 7500 um or less, 1 mm or less, 5 mm or less, 10 mm or less, 100 mm or less, or 1000 mm or less, or in a range between any two of these values. | In the range of 1 mm to 10 mm; Or About 5 mm |

Hinge:

| Parameters | Embodiments | Preferred Embodiments |
|---|---|---|
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm$^2$ or less, 5 mm$^2$ or less, 10 mm$^2$ or less, 20 mm$^2$ or less, 30 mm$^2$ or less, 40 mm$^2$ or less, 50 mm$^2$ or less, 100 mm$^2$ or less, 200 mm$^2$ or less, 500 mm$^2$ or less, or in a range between any of the two values | In the range of 20 to 200 mm$^2$; or about 120 mm$^2$ |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, | In the range of 90 to 180 degrees |

-continued

| Parameters | Embodiments | Preferred Embodiments |
|---|---|---|
| | 270 or less, 285 or less, 300 or less, 315 or less, 330 or less, 345 or less or 360 or less degrees, or in a range between any two of these values | |
| No. of Layers | 1, 2, 3, 4, 5, or more | 1 or 2 |
| Layer thickness | 0.1 um or less, 1 um or less, 2 um or less, 3 um or less, 5 um or less, 10 um or less, 20 um or less, 30 um or less, 50 um or less, 100 um or less, 200 um or less, 300 um or less, 500 um or less, 1 mm or less, 2 mm or less, and a range between any two of these values | In the range of 20 um to 1 mm; or Around 50 um |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

Notch:

| Parameters | Embodiments | Preferred Embodiments |
|---|---|---|
| Number | 1, 2, 3, 4, 5, or more | 1 or 2 |
| Shape | round, ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm; or about 10 mm |
| Area | 1 $mm^2$ (square millimeter) or less, 10 $mm^2$ or less, 25 $mm^2$ or less, 50 $mm^2$ or less, 75 $mm^2$ or less or in a range between any two of these values. | In the range of 10 to 150 $mm^2$; or about 50 $mm^2$ |

Trench:

| Parameters | Embodiments | Preferred Embodiments |
|---|---|---|
| Number | 1, 2, 3, 4, 5, or more | 1 or 2 |
| Shape | Closed (round, ellipse, rectangle, triangle, polygon, ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 $mm^2$ or less, 0.005 $mm^2$ or less, 0.01 $mm^2$ or less, 0.05 $mm^2$ or less, 0.1 $mm^2$ or less, 0.5 $mm^2$ or less, 1 $mm^2$ or less, 2 $mm^2$ or less, 5 $mm^2$ or less, 10 $mm^2$ or less, 20 $mm^2$ or less, or in a range between any two of these values. | |
| Volume | 0.1 uL or more, 0.5 uL or more, 1 uL or more, 2 uL or more, 5 uL or more, 10 uL or more, 30 uL or more, 50 uL or more, 100 uL or more, 500 uL or more, 1 mL or more, or in a range between any two of these values | In the range of 1 uL to 20 uL; or About 5 uL |

Receptacle Slot

| Parameters | Embodiments | Preferred Embodiments |
|---|---|---|
| Shape of receiving area | round, ellipse, rectangle, triangle, polygon, ring-shaped, or any superposition of these shapes; | |

| Parameters | Embodiments | Preferred Embodiments |
|---|---|---|
| Difference between sliding track gap size and card thickness | 100 nm, 500 nm, 1 um, 2 um, 5 um, 10 um, 50 um, 100 um, 300 um, 500 um, 1 mm, 2 mm, 5 mm, 1 cm, or in a range between any two of the values. | In the range of 50 to 300 um; or about 75 um |
| Difference between receiving area and card area | 1 mm$^2$ (square millimeter) or less, 10 mm$^2$ or less, 25 mm$^2$ or less, 50 mm$^2$ or less, 75 mm$^2$ or less, 1 cm$^2$ (square centimeter) or less, 2 cm$^2$ or less, 3 cm$^2$ or less, 4 cm$^2$ or less, 5 cm$^2$ or less, 10 cm$^2$ or less, 100 cm$^2$ or less, or in a range between any of the two values. | |

9. Hand Pressing

For the devices, apparatus, systems, and methods herein disclosed, human hands can be used for manipulating or handling or the plates and/or samples. In some embodiments, human hands can be used to press the plates into a closed configuration; In some embodiments, human hands can be used to press the sample into a thin layer. The manners in which hand pressing is employed are described and/or summarized in PCT Application (designating U.S.) Nos. PCT/US2016/046437 filed on Aug. 10, 2016 and PCT/US2016/051775 filed on Sep. 14, 2016, and in US Provisional Application Nos. 62/431,639 filed on Dec. 9, 2016, 62/456,287 filed on Feb. 8, 2017, 62/456,065 filed on Feb. 7, 2017, 62/456,504 filed on Feb. 8, 2017, and 62/460,062 filed on Feb. 16, 2017, which are all hereby incorporated by reference by their entireties.

In some embodiments, human hand can be used to manipulate or handle the plates of the QMAX device. In certain embodiments, the human hand can be used to apply an imprecise force to compress the plates from an open configuration to a closed configuration. In certain embodiments, the human hand can be used to apply an imprecise force to achieve high level of uniformity in the thickness of the sample (e.g. less than 5%, 10%, 15%, or 20% variability).

In some embodiments, the plates are movable relative to each other into different configurations, including an open configuration and a closed configuration. In the open configuration, the two plates are partially or completely separated apart, the spacing between the plates is not regulated by the spacers, and the sample is deposited on one or both of the plates. In the closed configuration, at least part of the sample is compressed by the two plates into a layer of highly uniform thickness and is substantially stagnant relative to the plates, wherein the uniform thickness of the layer is confined by the sample contact areas of the two plates and is regulated by the plates and the spacers. In some embodiments, the force that presses the two plates into the closed configuration is an imprecise pressing force provided by human hand.

In some embodiments, the plates are conformably pressed. Conformable pressing refers to pressing, in certain embodiments by human hand, either in parallel or sequentially, an area of at least one of the plates to press the plates together to a closed configuration, wherein the conformable pressing generates a substantially uniform pressure on the plates over the at least part of the sample, and the pressing spreads the at least part of the sample laterally between the sample contact surfaces of the plates, and wherein the closed configuration is a configuration in which the spacing between the plates in the layer of uniform thickness region is regulated by the spacers. In certain embodiments, a conformable pressing is a method that makes the pressure applied over an area is substantially constant regardless the shape variation of the outer surfaces of the plates. In certain embodiments, parallel pressing applies the pressures on the intended area at the same time, and a sequential pressing applies the pressure on a part of the intended area and gradually move to other area.

In some embodiments, the plates are pressed into a closed configuration by an imprecise force. In certain embodiments, the imprecise force is applied by human hand. In some embodiments, the force is an imprecise force that has a magnitude which is, at the time that the force is applied, either (a) unknown and unpredictable, or (b) cannot be known and cannot be predicted within an accuracy equal or better than 30% of the force applied. In some embodiments, the force is an imprecise force that has a magnitude which cannot, at the time that the force is applied, be determined within an accuracy equal or better than 30%, 40%, 50%, 70%, 100%, 200%, 300%, 500%, 1000%, 2000%, or any range between the two values.

10. Smartphone

The devices, apparatus, systems, and methods herein disclosed can be used with a mobile device, such as but not limited to a smartphone. The smartphone detection technology is herein disclosed, or listed, described, and/or summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the smartphone comprises a camera, which can be used to capture images or the sample when the sample is positioned in the field of view of the camera (e.g. by an adaptor). In certain embodiments, the camera includes one set of lenses (e.g. as in iPhone™ 6). In certain embodiments, the camera includes at least two sets of lenses (e.g. as in iPhone™ 7). In some embodiments, the smartphone comprises a camera, but the camera is not used for image capturing.

In some embodiments, the smartphone comprises a light source such as but not limited to LED (light emitting diode). In certain embodiments, the light source is used to provide illumination to the sample when the sample is positioned in the field of view of the camera (e.g. by an adaptor). In some embodiments, the light from the light source is enhanced, magnified, altered, and/or optimized by optical components of the adaptor.

In some embodiments, the smartphone comprises a processor that is configured to process the information from the sample. The smartphone includes software instructions that, when executed by the processor, can enhance, magnify, and/or optimize the signals (e.g. images) from the sample. The processor can include one or more hardware components, such as a central processing unit (CPU), an application-specific integrated circuit (ASIC), an application-specific instruction-set processor (ASIP), a graphics processing unit (GPU), a physics processing unit (PPU), a digital signal processor (DSP), a field-programmable gate array (FPGA), a programmable logic device (PLD), a controller, a microcontroller unit, a reduced instruction-set computer (RISC), a microprocessor, or the like, or any combination thereof.

In some embodiments, the smartphone comprises a communication unit, which is configured and/or used to transmit data and/or images related to the sample to another device. Merely by way of example, the communication unit can use a cable network, a wireline network, an optical fiber network, a telecommunications network, an intranet, the Internet, a local area network (LAN), a wide area network (WAN), a wireless local area network (WLAN), a metropolitan area network (MAN), a wide area network (WAN), a public telephone switched network (PSTN), a Bluetooth network, a ZigBee network, a near field communication (NFC) network, or the like, or any combination thereof.

In some embodiments, the smartphone is an iPhone™, an Android™ phone, or a Windows™ phone.

11. Cloud

The devices, apparatus, systems, and methods herein disclosed can be used with cloud storage and computing technologies. The related cloud technologies are herein disclosed, or listed, described, and summarized in PCT Application (designating U.S.) Nos. PCT/US2016/045437 and PCT/US0216/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein in their entireties for all purposes.

In some embodiments, the cloud storage and computing technologies can involve a cloud database. Merely by way of example, the cloud platform can include a private cloud, a public cloud, a hybrid cloud, a community cloud, a distributed cloud, an inter-cloud, a multi-cloud, or the like, or any combination thereof. In some embodiments, the mobile device (e.g. smartphone) can be connected to the cloud through any type of network, including a local area network (LAN) or a wide area network (WAN).

In some embodiments, the data (e.g. images of the sample) related to the sample is sent to the cloud without processing by the mobile device and further analysis can be conducted remotely. In some embodiments, the data related to the sample is processed by the mobile device and the results are sent to the cloud. In some embodiments, both the raw data and the results are transmitted to the cloud.

What is claimed is:

1. A method for examining an effect of a test reagent on one or more microorganism individuals in a sample, the method comprising:
(a) putting the test reagent, the sample, and a detection agent between two plates, wherein the detection agent is a fluorescence stain dye that labels a microorganism individual, and wherein one or both plates have spacers, and each of the plates has a sample contact surface;
(b) compressing the plates to form a uniform testing layer;
(c) using an imager to acquire, at at least two discrete time points, images of signals emanating from the microorganism individual in the uniform testing layer; and
(d) analyzing the images at the at least two discrete time points to determine a change of the microorganism individual between the at least two discrete time points;
wherein the two plates are movable relative to each other into different configurations, including an open configuration and a closed configuration, and at least one of the two plates is a flexible plate;
wherein the spacers have an inter-spacer distance (ISD) of 500 μm or less, the fourth power of the inter-spacer distance (ISD) divided by thickness (h) and Young's modulus (E) of the flexible plate ($ISD^4/(hE)$) is $5 \times 10^5$ μm$^3$/GPa or less, and the thickness of the flexible plate times the Young's modulus of the flexible plate is in the range of 60 to 750 GPa-μm,
wherein in the open configuration, the two plates are partially or entirely separated apart, the spacing between the plates is not regulated by the spacers, and the sample is deposited on one or both of the plates;
wherein in the closed configuration, which is configured after deposition of the sample in the open configuration: at least part of the sample is compressed by the two plates into the uniform testing layer having a highly uniform thickness, and the uniform thickness of the layer is confined by the sample contact surfaces of the plates and is regulated by the plates and the spacers;
wherein at least one of the spacers is inside the sample contact surface of one or both of the plates,
wherein the imaging is in the closed configuration, and wherein the thickness of the testing layer at the closed configuration is configured such that there is substantially no overlap between any two microorganism individuals; and
wherein in the closed configuration, the thickness of the uniform testing layer is regulated by the two plates and the spacers within the sample area, and the height of the spacers is 250 microns or less.

2. A method for examining an effect of a drug on one or more microorganism individuals in a sample, the method comprising:
(a) putting a drug and a sample containing one or more microorganism individuals between two plates to form a uniform testing layer;
(b) acquiring, using an imager, at least two images of the uniform testing layer at discrete time points;
(c) analyzing the images to determine a change of the one or more microorganism individuals between at least two of the discrete time points;
wherein the thickness of the uniform testing layer is regulated by the two plates and spacers inside of the sample and between the two plates;
wherein the thickness of the testing layer is configured such that there is substantially no overlap between two microorganism individuals;
wherein the two plates are movable relative to each other into different configurations, including an open configuration and a closed configuration;
wherein each of the plates has a sample contact surface;
wherein in the open configuration, the two plates are partially or entirely separated apart, the spacing between the plates is not regulated by the spacers, and the sample is deposited on one or both of the plates;
wherein in the closed configuration, which is configured after deposition of the sample in the open configuration: at least part of the sample is compressed by the two plates into the uniform testing layer having a highly uniform thickness, and the uniform thickness of the layer is confined by the sample contact surfaces of the plates and is regulated by the plates and the spacers, wherein at least one of the two plates is a flexible plate; wherein the spacers have an inter-spacer distance (ISD) of 500 µm or less, the fourth power of the inter-spacer distance (ISD) divided by thickness (h) and Young's modulus (E) of the flexible plate (ISD$^4$/(hE) is 5×10$^5$ µm$^3$/GPa or less, and the thickness of the flexible plate times the Young's modulus of the flexible plate is in the range of 60 to 750 GPa-µm, and wherein at least one of the spacers are inside the sample contact surface of one or both of the plates.

3. The method of claim 2, further comprising a step of staining a microorganism using a cell viability dye that indicates whether a stained cell is alive or dead.

4. The method of claim 2, further comprising an additional reagent that stains the microorganism individual.

5. The method of claim 4, wherein the detection agent or the additional reagent or the test agent are coated on one or both of the plates before depositing the sample.

6. The method of claim 2, wherein the one or more microorganisms are selected from the group consisting of bacteria, fungi, archaea, viruses, protists, micro-animals, myxozoa, arthropods, crustaceans, and microscopic nematodes.

7. The method of claim 2, wherein the one or more microorganisms are selected from a genus, and the genus is selected from the group consisting of *Bacillus, Bartonella, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia*.

8. The method of claim 2, wherein the one or more microorganisms are selected from the group consisting of *Bacillus anthracis, Bacillus cereus, Bartonella henselae, Bartonella Quintana, Bordetella pertussis, Borrelia burgdorferi, Borrelia garinii, Borrelia afzelii, Borrelia recurrentis, Brucella abortus, Brucella canis, Brucella melitensis, Brucella suis, Campylobacter jejuni, Chlamydia pneumoniae, Chlamydia trachomatis, Chlamydophila psittaci, Clostridium botulinum, Clostridium difficile, Clostridium perfringens, Clostridium,* etani, *Corynebacterium diphtherias, Enterococcus faecalis, Enterococcus faecium, Escherichia coli, Francisella tularensis, Haemophilus influenzae, Helicobacter pylori, Legionella,* neumophila, *Leptospira interrogans, Leptospira santarosai, Leptospira weilii, Leptospira noguchii, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsia, Salmonella typhi, Salmonella typhimurium, Shigella sonnei, Staphylococcus aureus, Staphylococcus epidermidis, Staphylococcus saprophyticus, Streptococcus agalactiae, Streptococcus,* neumoniae, *Streptococcus pyogenes, Treponema pallidum, Ureaplasma urealyticum, Vibrio cholerae, Yersinia pestis, Yersinia enterocolitica,* and *Yersinia pseudotuberculosis*.

9. The method of claim 2, wherein the drug is selected from the group consisting of an antibiotic, and an antifungal reagent.

10. The method of claim 9, wherein the drug comprises an antibiotic, and wherein the antibiotic is selected from the group consisting of Actinomycin D, Actinonin, Aculeacin A, Acycloguanosine, Adenine 9-β-D-arabinofuranoside, Alamethicin, Alamethicin, L-Alanyl-L-1-aminoethylphosphonic acid, Albendazole, 17-(Allylamino)-17-demethoxygeldanamycin, Amastatin, Amikacin, Amikacin, 7-Aminoactinomycin D, 7-Aminocephalosporanic acid, N-(6-Aminohexyl)-5-chloro-1-naphthalenesulfonamide, (+)-6-Aminopenicillanic acid, Amoxicillin, Amphotericin B, Ampicillin, Anhydroerythromycin A, Anisomycin, Antimycin A, Antimycin A2, Antipain, Aphidicolin, Apicidin, Apoptolidin A, Apramycin, Artesunate, Ascochlorin, Ascomycin, 5-Azacytidine, Azaserine, Azithromycin, Azlocillin, Bacitracin, Bactenecin, Bafilomycin A1, Bafilomycin B1, Bestatin, Beta D-4 human recombinant, Beta D-1 (36 aa) human recombinant, Beta D-1 (47 aa) human recombinant, Bithionol VETRANAL™, Blasticidine S, Bleomycin, BM-Cyclin, Borrelidin, Brefeldin A, Caerulomycin A, Calcium ionophore III Selectophore™, Calcium Ionophore A23187, Calcium Ionophore A23187, Calcium Ionophore A23187, (S)-(+)-Camptothecin, Capreomycin, Carbadox, Carbenicillin, Carboplatin, Cecropin A, Cecropin B, Cecropin P1 Porcine, Cefaclor, Cefalexin VETRANAL™, Cefazoli, Cefixime, Cefmetazole, Cefoperazone, Cefotaxime, Cefsulodin, Ceftazidime, Ceftriaxone, Cephalexin, Cephalomannine, Cephalothin, Cephradine, Cercosporin, Cerulenin, Cetylpyridinium, Chloramphenicol, Chlorhexidine, Chloroquine, Chlortetracycline, Chromomycin A3, Chrysomycin A, Chrysomycin B, Cinnamycin, Cinoxacin, Ciprofloxacin, Clarithromycin, Clebopride, Clindamycin, Clofazimine, Clotrimazole, Cloxacillin, Colistin, Colominic acid, Compound 48/80, Concanamycin A, Cordycepin, Coumermycin A1, Cryptotanshinone, Crystal Violet, Cycloheximide, D-Cycloserine, Cyclosporin A, Cyclosporin C, Cytochalasin D, Cytochalasin B, Dacarbazine antineoplastic purine analog, Daunorubicin, 10-Deacetylbaccatin III, Decoyinine, Defensin HNP-1, Defensin HNP-2, Demeclocycline, 1-Deoxymannojirimycin, 1-Deoxynojirimycin, cis-Diamineplatinum(II), 6,9-Diamino-2-ethoxyacridine-DL-lactate, cis-Diammineplatinum(II), 6-Diazo-5-oxo-L-norleucine, 5,7-Dichloro-8-hydroxy-2-methylquinoline, Dichlorophene PESTANAL®, Dicloxacillin, Diethylcarbamazine, Diethylcarbamazine, Difloxacin, Dihydrostreptomycin, Dihydrostreptomycin, Diloxanide furoate, Dimetridazole, Dirithromycin, Doxorubicin, Doxycycline, Duramycin, Econazole, Elafin, Embelin, Emetine, Enrofloxacin, Erythromycin, Ethambutol, Etoposide, Fengycin, Filipin, Florfenicol, Flubendazol VETRANAL™, Fluconazole, Flumequine, Flumethasone, 5-Fluorocytosine nucleoside analog, Flurbiprofen cyclooxygenase inhibitor, Formycin A, Fumagillin, Fumitremorgin C, Furazolidone, Fusaric acid, G 418, Ganciclovir, Gatifloxacin, Geldanamycin, Gentamicin, Gentamicin, Gentian Violet, Gliotoxin, Gramicidins, Griseofulvin, Herbimycin A, Hexadecylpyridinium, Honokiol, Hydrocortisone 21, 8-Hydroxyquinoline, 4-Hydroxytamoxifen, (Z)-4-Hydroxytamoxifen, Hygromycin B, Ikarugamycin, Imipenem, Indomethacin, Indomethacin, Ionomycin, Irgasan, Itraconazole, Iturin A, Ivermectin, Josamycin, K-252a, K-252b, Kanamycins, Kasugamycin, Kendomycin, Ketoconazole, Kirromycin, L-(+)-Lactic acid, Lactoferricin B, Leptomycin A, Leptomycin B, Levamisol, Levofloxacin, Lincomycin, *Listeria* mono Selective Supplement I, LL-37, Lomefloxacin, Lysostaphin, Magainin I, Mebendazole, Meclocycline, Menadione, 2-Mercaptopyridine N-oxide, N-Methyl-1-deoxynojirimycin, 2-Methyl-4-isothiazolin-3-one hydrochloride, Metronidazole, Mevastatin, (±)-Miconazole, Minocycline, Mithramycin A, Mitomycin C, Monensin, Morantel, Moxalactam, Mupirocin, Mycosubtilin, Myxothiazol, Prothionamide, Nafcillin, Naftifine, Nalidixic acid, Narasin, Neocarzinostatin, Neomycin, Netilmicin, Netropsin, Niclosamide, Nigericin, Nikkomycin Z, Nisin, Nitrofurantoin, Nogalamycin, Nonactin, Norfloxacin, Nourseothricin, Novobiocin, NP-1, Nystatin, Ochratoxin A, Ofloxacin, Oligomycin, Oligomycin A, Oxacillin, Oxantel, Oxolinic acid quinolone, Oxytetracycline, Oxytetra, Paclitaxel, Paromomycin, Patulin, PD 404,182, Pediocin, Pefloxacin, D-Penicillamine, Penicillin G, Penicillin V, Pentamidine, PGLa, 1,10-Phenanthroline, Phenazine, Phenoxymethylpenicillinic acid, Phleomycin, Phosphomycin, Pimaricin, Pipemidic acid, Piperacillin, Pirarubicin, Platensimycin, Polymyxin B, Poly(vinylpyrrolidone)-Iodine complex, Potassium clavulanate: cellulose (1:1), Potassium Sorbate, Praziquantel, Puromycin, Pyrantel, Pyrazinecarboxamide, Pyronaridine, Pyrrolnitrin, Quinine, 8-Quinolinol, Radicicol, Ramoplanin, Rapamycin, Rebeccamycin, Reveromycin A, Ribavirin, Ribostamycin, Ricobendazole, Rifabutin, Rifampicin, Rifamycin SV, Rifapentine, Rifaximin, Ristomycin, Rolitetracycline, Roxithromycin, Salinomycin, Sangivamycin, Sinefungin, Sisomicin, Sorbic acid, Sordarin, Sparfloxacin, Spectinomycin, Spergualin, Spiramycin, Staurosporine, Streptolysin O, Streptomycin, Streptonigrin, Streptozocin, Succinylsulfathiazole, Sulconazole, Sulfabenzamide, Sulfachloropyridazine, Sulfadiazine, Sulfadimethoxine, Sulfadimidine, Sulfadoxin, Sulfaguanidine, Sulfameter, Sulfamethazine, Sulfamonomethoxine, Sulfanilamide, Sulfanitran, Sulfaquinoxaline, Sulfasalazine, Sulfathiazole, Sulochrin, Surfactin, Swainsonine, Syringomycin E, Tamoxifen, Tazobactam, Teicoplanin, Terbinafine, Terconazole, Tetracycline, Tetramisole, Thiabendazole, Thiamphenicol, Thimerosal, Thiolutin, Thiostrepton, Thio-TEPA, Thymol, Tiamulin, Ticarcillin, Tioconazole, Tobramycin, Aminoglycoside antibiotic, Tobramycin, Tolnaftate, Toyocamycin, Triacsin C, Trichlorfon, Trimethoprim, Tubercidin, Tunicamycin, Tunicamycin C2 homolog, Tylosin, Valacyclovir, Valinomycin, Vinblastine, Virginiamycin S1, Virginiamycin M1, an analog thereof, a salt thereof, and a derivative thereof.

11. The method of claim 9, wherein the drug comprises an antifungal reagent, and wherein the antifungal reagent is selected from the group consisting of Polyene anti fungal, Imidazole, Triazole, Thiazole, Echinocandin, Aurone, Benzoic acid, Ciclopirox, Flucytosine and 5-fluorocytosine, Griseofulvin, Haloprogin, Tolnaftate, Undecylenic acid, Crystal violet, Balsam of Peru, an analog thereof, a salt thereof, and a derivative thereof.

12. The method of claim 2, wherein the imager comprises a camera.

13. The method of claim 2, wherein the imager comprises a video camera.

14. The method of claim 2, wherein the uniform height of the spacers is equal to or less than an average dimension of the one or more microorganisms.

15. The method of claim 2, wherein the uniform height of the spacers is in the range of 75% to 125% of an average dimension of the one or more microorganisms.

16. The method of claim 2, wherein at least one of the plates is transparent.

17. The method of claim 2, wherein one or both of the plates comprise, on the respective sample contact area, a dye that, upon contacting the sample, is dissolved in the sample and stains the one or more microorganisms.

18. The method of claim 2, wherein the sample comprises reagents that facilitate the survival and/or division of the one or more microorganisms.

19. The method of claim 2, wherein one or both of the plates comprise, on the respective sample contact area, reagents that facilitate the survival and/or division of the microorganism.

20. The method of claim 2, further comprising a housing configured to hold the sample and to be mounted to a mobile communication device.

21. The method of claim 2, wherein the imager is configured to acquire a series of images of the microorganism at discrete time points.

22. The method of claim 2, further comprising a processor configured to receive and analyze the series of images, identify and count the microorganism in a first area of each of the images.

23. The method of claim 2, wherein the imager is configured to acquire a video that comprises a series of images of the microorganisms over a first time period.

24. The method of claim 20, wherein the housing comprises optics for facilitating the imaging and/or signal processing of the sample by a mobile communication device, and a mount configured to hold the optics on the mobile communication device.

25. The method of claim 24, wherein the mobile communication device is configured to communicate test results to a medical professional, a medical facility or an insurance company.

26. The method of claim 25, wherein the mobile communication device is further configured to communicate information on the subject with the medical professional, medical facility or insurance company.

27. The method of claim 26, wherein the mobile communication device is configured to receive a prescription, diagnosis or a recommendation from a medical professional.

28. The method of claim 26, wherein the mobile communication device communicates with the remote location via a wifi or cellular network.

29. The method of claim 24, wherein the mobile communication device is a mobile phone.

30. The method of claim 2, wherein the one or more microorganisms have an average dimension of less than 1 mm.

31. The method of claim 2, wherein one or both of the plates comprise, on the respective sample contact area, a control zone and an experimental zone, wherein the experimental zone comprises one or more test reagents that, upon contacting the sample, are dissolved and diffuses in the sample, and wherein the control zone comprises no such test reagents.

32. The method of claim 2, further comprising contacting the sample with an additional reagent, wherein the additional reagent comprises at least one selected from the group consisting of staining dyes to label the microorganisms, life-supportive reagents to facilitate the survival of the microorganisms, and proliferative reagents to maintain or facilitate the proliferation of the microorganisms.

33. The method of claim 32, wherein the additional reagent comprises a staining dye,
wherein the staining dye comprises a fluorescent molecule selected from the group consisting of IRDye800CW, Alexa 790, Dylight 800, fluorescein, fluorescein isothiocyanate, succinimidyl esters of carboxyfluorescein, succinimidyl esters of fluorescein, 5-isomer of fluorescein dichlorotriazine, caged carboxyfluorescein-alanine-carboxamide, Oregon Green 488, Oregon Green 514; Lucifer Yellow, acridine Orange, rhodamine, tetramethylrhodamine, Texas Red, propidium iodide, JC-1 (5,5',6,6'-tetrachloro-1,1',3,3'-tetraethylbenzimidazoylcarbocyanine iodide), tetrabromorhodamine 123, rhodamine 6G, TMRM (tetramethyl rhodamine methyl ester), TMRE (tetramethyl rhodamine ethyl ester), tetramethylrosamine, rhodamine B and 4-dimethylaminotetramethylrosamine, green fluorescent protein, blue-shifted green fluorescent protein, cyanshifted green fluorescent protein, redshifted green fluorescent protein, yellow-shifted green fluorescent protein, 4-acetamido-4'-isothiocyanatostilbene-2,2'disulfonic acid; acridine and derivatives, such as acridine, acridine isothiocyanate; 5-(2'-aminoethyl)aminonaphthalene-1-sulfonic acid (EDANS); 4-amino-N-[3-vinylsulfonyl)phenyl]naphth-alimide-3,5 disulfonate; N-(4-anilino-1-naphthyl)maleimide; anthranilamide; 4,4-difluoro-5-(2-thienyl)-4-bora-3a,4a diaza-5-indacene-3-propioni-c acid BODIPY; cascade blue; Brilliant Yellow; coumarin and derivatives: coumarin, 7-amino-4-methylcoumarin (AMC, Coumarin 120),7-amino-4-trifluoromethylcoumarin (Coumarin 151); cyanine dyes; cyanosine; 4',6-diaminidino-2-phenylindole (DAPI); 5',5"-dibromopyrogallol sulfonaphthalein (Bromopyrogallol Red); 7-diethylamino-3-(4'-isothiocyanatophenyl)-4-methylcoumarin; diethylenetriaamine pentaacetate; 4,4'-diisothiocyanatodihydro-stilbene-2-,2'-disulfonic acid; 4,4'-diisothiocyanatostilbene-2,2'-disulfonic acid; 5-(dimethylamino]naphthalene-1-sulfonyl chloride (DNS, dansylchloride); 4-dimethylaminophenylazophenyl-4'-isothiocyanate (DABITC); eosin and derivatives: eosin, eosin isothiocyanate, erythrosin and derivatives: erythrosin B, erythrosin, isothiocyanate; ethidium; fluorescein and derivatives: 5-carboxyfluorescein (FAM), 5-(4,6-dichlorotriazin-2-yl)amino--fluorescein (DTAF), 2',7'dimethoxy-4'5'-dichloro-6-carboxyfluorescein (JOE), fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; ophthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of 5 sulforhodamine (Texas Red); N,N,N', N'-tetramethyl-6-carboxyrhodamine (TAMRA); tetramethyl rhodamine; tetramethyl hodamine isothiocyanate (TRITC); riboflavin; 5-(2'-aminoethyl) aminonaphthalene-1-sulfonic acid (EDANS), 4-(4'-dimethylaminophenylazo)benzoic acid (DABCYL), rosolic acid; CAL Fluor Orange 560; terbium chelate derivatives; Cy 3; Cy 5; Cy 5.5; Cy 7; IRD 700; IRD 800; La Jolla Blue; phthalo cyanine; and naphthalo cyanine, coumarins and related dyes, xanthene dyes such as rhodols, resorufins, bimanes, acridines, isoindoles, dansyl dyes, aminophthalic hydrazides such as luminol, and isoluminol derivatives, aminophthalimides, aminonaphthalimides, aminobenzofurans, aminoquinolines, dicyanohydroquinones, fluorescent europium and terbium complexes, and combinations thereof.

34. The method of claim 2, further comprising a life-supportive reagent that facilitates the survival of the microorganisms.

35. The method of claim 11, wherein the Polyene anti fungal is selected from the group consisting of Amphotericin B, Candicidin, Filipin, Hamycin, Natamycin, Nystatin, Rimocidin, and a combination thereof,
the Imidazole is selected from the group consisting of Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, and a combination thereof,
the Triazoles is selected from the group consisting of Albaconazole, Efinaconazole, Epoxiconazole, Fluconazole, Isavuconazole, Itraconazole, Posaconazole, Propiconazole, Ravuconazole, Terconazole, Voriconazole, and a combination thereof,
the Thiazole comprises Abafungin,
the Allylamine is selected from the group consisting of Amorolfin, Butenafine, Naftifine, Terbinafine, and a combination thereof, and
the Echinocandin is selected from the group consisting of Anidulafungin, Caspofungin, Micafungin, and a combination thereof.

36. The method of claim 32, wherein the staining dyes comprises cell viability dyes,
the life-supportive reagents comprise nutrients, oxygen source, pH buffer, or a combination thereof, and
the proliferative reagents comprise hormones, siderophore, or a combination thereof.

37. The method of claim 32, wherein the additional reagent comprises a staining dye selected from the group consisting of a fluorescent protein, a chromogenic protein, and a combination thereof.

38. The method of claim 37, wherein the fluorescent protein is a green fluorescent protein (GFP).

39. The method of claim 38, wherein the GFP is a GFP derived from *Aequoria victoria*.

40. The method of claim 38, wherein the GFP is a humanized or enhanced GFP.

41. The method of claim 38, wherein the GFP is from *Renilla reniformis, Renilla mulleri*, or *Ptilosarcus guernyi*.

42. The method of claim 37, wherein the fluorescent protein or chromogenic protein is from *Anthozoan* species.

43. The method of claim 2, further comprising contacting the sample with an additional reagent, wherein the additional reagent comprises a staining dye that is a cell viability dye.

44. The method of claim 1, wherein the two plates are connected to a hinge that controls the rotation of the two plates.

45. The method of claim 2, wherein the two plates are connected to a hinge that controls the rotation of the two plates.

46. The method of claim 1, wherein the spacers have a height in a range from 1 μm to 100 μm.

47. The method of claim 2, wherein the spacers have a height in a range from 1 to 100 μm.

48. The method of claim 1, wherein the test reagent comprises an antibiotic, and wherein the antibiotic is selected from the group consisting of Actinomycin D, Actinonin, Aculeacin A, Acycloguanosine, Adenine 9-β-D-arabinofuranoside, Alamethicin, Alamethicin, L-Alanyl-L-1-aminoethylphosphonic acid, Albendazole, 17-(Allylamino)-17-demethoxygeldanamycin, Amastatin, Amikacin, Amikacin, 7-Aminoactinomycin D, 7-Aminocephalosporanic acid, N-(6-Aminohexyl)-5-chloro-1-naphthalenesulfonamide, (+)-6-Aminopenicillanic acid, Amoxicillin, Amphotericin B, Ampicillin, Anhydroerythromycin A, Anisomycin, Antimycin A, Antimycin A2, Antipain, Aphidicolin, Apicidin, Apoptolidin A, Apramycin, Artesunate, Ascochlorin, Ascomycin, 5-Azacytidine, Azaserine, Azithromycin, Azlocillin, Bacitracin, Bactenecin, Bafilomycin A1, Bafilomycin B1, Bestatin, Beta D-4 human recombinant, Beta D-1 (36 aa) human recombinant, Beta D-1 (47 aa) human recombinant, Bithionol VETRANAL™, Blasticidine S, Bleomycin, BM-Cyclin, Borrelidin, Brefeldin A, Caerulomycin A, Calcium ionophore III Selectophore™, Calcium Ionophore A23187, Calcium Ionophore A23187, Calcium Ionophore A23187, (S)-(+)-Camptothecin, Capreomycin, Carbadox, Carbenicillin, Carboplatin, Cecropin A, Cecropin B, Cecropin P1 Porcine, Cefaclor, Cefalexin VETRANAL™, Cefazoli, Cefixime, Cefmetazole, Cefoperazone, Cefotaxime, Cefsulodin, Ceftazidime, Ceftriaxone, Cephalexin, Cephalomannine, Cephalothin, Cephradine, Cercosporin, Cerulenin, Cetylpyridinium, Chloramphenicol, Chlorhexidine, Chloroquine, Chlortetracycline, Chromomycin A3, Chrysomycin A, Chrysomycin B, Cinnamycin, Cinoxacin, Ciprofloxacin, Clarithromycin, Clebopride, Clindamycin, Clofazimine, Clotrimazole, Cloxacillin, Colistin, Colominic acid, Compound 48/80, Concanamycin A, Cordycepin, Coumermycin A1, Cryptotanshinone, Crystal Violet, Cycloheximide, D-Cycloserine, Cyclosporin A, Cyclosporin C, Cytochalasin D, Cytochalasin B, Dacarbazine antineoplastic purine analog, Daunorubicin, 10-Deacetylbaccatin III, Decoyinine, Defensin HNP-1, Defensin HNP-2, Demeclocycline, 1-Deoxymannojirimycin, 1-Deoxynojirimycin, cis-Diamineplatinum(II), 6,9-Diamino-2-ethoxyacridine-DL-lactate, cis-Diammineplatinum (II), 6-Diazo-5-oxo-L-norleucine, 5,7-Dichloro-8-hydroxy-2-methylquinoline, Dichlorophene PESTANAL®, Dicloxacillin, Diethylcarbamazine, Diethylcarbamazine, Difloxacin, Dihydrostreptomycin, Dihydrostreptomycin, Diloxanide furoate, Dimetridazole, Dirithromycin, Doxorubicin, Doxycycline, Duramycin, Econazole, Elafin, Embelin, Emetine, Enrofloxacin, Erythromycin, Ethambutol, Etoposide, Fengycin, Filipin, Florfenicol, Flubendazol VETRANAL™, Fluconazole, Flumequine, Flumethasone, 5-Fluorocytosine nucleoside analog, Flurbiprofen cyclooxygenase inhibitor, Formycin A, Fumagillin, Fumitremorgin C, Furazolidone, Fusaric acid, G 418, Ganciclovir, Gatifloxacin, Geldanamycin, Gentamicin, Gentamicin, Gentian Violet, Gliotoxin, Gramicidins, Griseofulvin, Herbimycin A, Hexadecylpyridinium, Honokiol, Hydrocortisone 21, 8-Hydroxyquinoline, 4-Hydroxytamoxifen, (Z)-4-Hydroxytamoxifen, Hygromycin B, Ikarugamycin, Imipenem, Indomethacin, Indomethacin, Ionomycin, Irgasan, Itraconazole, Iturin A, Ivermectin, Josamycin, K-252a, K-252b, Kanamycins, Kasugamycin, Kendomycin, Ketoconazole, Kirromycin, L-(+)-Lactic acid, Lactoferricin B, Leptomycin A, Leptomycin B, Levamisol, Levofloxacin, Lincomycin, *Listeria* mono Selective Supplement I, LL-37, Lomefloxacin, Lysostaphin, Magainin I, Mebendazole, Meclocycline, Menadione, 2-Mercaptopyridine N-oxide, N-Methyl-1-deoxynojirimycin, 2-Methyl-4-isothiazolin-3-one hydrochloride, Metronidazole, Mevastatin, (±)-Miconazole, Minocycline, Mithramycin A, Mitomycin C, Monensin, Morantel, Moxalactam, Mupirocin, Mycosubtilin, Myxothiazol, Prothionamide, Nafcillin, Naftifine, Nalidixic acid, Narasin, Neocarzinostatin, Neomycin, Netilmicin, Netropsin, Niclosamide, Nigericin, Nikkomycin Z, Nisin, Nitrofurantoin, Nogalamycin, Nonactin, Norfloxacin, Nourseothricin, Novobiocin, NP-1, Nystatin, Ochratoxin A, Ofloxacin, Oligomycin, Oligomycin A, Oxacillin, Oxantel, Oxolinic acid quinolone, Oxytetracycline, Oxytetra, Paclitaxel, Paromomycin, Patulin, PD 404,182, Pediocin, Pefloxacin, D-Penicillamine, Penicillin G, Penicillin V, Pentamidine, PGLa, 1,10-Phenanthroline, Phenazine, Phenoxymethylpenicillinic acid, Phleomycin, Phosphomycin, Pimaricin, Pipemidic acid, Piperacillin, Pirarubicin, Platensimycin, Polymyxin B, Poly (vinylpyrrolidone)-Iodine complex, Potassium clavulanate: cellulose (1:1), Potassium Sorbate, Praziquantel, Puromycin, Pyrantel, Pyrazinecarboxamide, Pyronaridine, Pyrrolnitrin, Quinine, 8-Quinolinol, Radicicol, Ramoplanin, Rapamycin, Rebeccamycin, Reveromycin A, Ribavirin, Ribostamycin, Ricobendazole, Rifabutin, Rifampicin, Rifamycin SV, Rifapentine, Rifaximin, Ristomycin, Rolitetracycline, Roxithromycin, Salinomycin, Sangivamycin, Sinefungin, Sisomicin, Sorbic acid, Sordarin, Sparfloxacin, Spectinomycin, Spergualin, Spiramycin, Staurosporine, Streptolysin O, Streptomycin, Streptonigrin, Streptozocin, Succinylsulfathiazole, Sulconazole, Sulfabenzamide, Sulfachloropyridazine, Sulfadiazine, Sulfadimethoxine, Sulfadimidine, Sulfadoxin, Sulfaguanidine, Sulfameter, Sulfamethazine, Sulfamonomethoxine, Sulfanilamide, Sulfanitran, Sulfaquinoxaline, Sulfasalazine, Sulfathiazole, Sulochrin, Surfactin, Swainsonine, Syringomycin E, Tamoxifen, Tazobactam, Teicoplanin, Terbinafine, Terconazole, Tetracycline, Tetramisole, Thiabendazole, Thiamphenicol, Thimerosal, Thiolutin, Thiostrepton, Thio-TEPA, Thymol, Tiamulin, Ticarcillin, Tioconazole, Tobramycin, Aminoglycoside antibiotic, Tobramycin, Tolnaftate, Toyocamycin, Triacsin C, Trichlorfon, Trimethoprim, Tubercidin, Tunicamycin, Tunicamycin C2 homolog, Tylosin, Valacyclovir, Valinomycin, Vinblastine, Virginiamycin S1, Virginiamycin M1, an analog thereof, a salt thereof, and a derivative thereof.

49. The method of claim 1, wherein the test reagent comprises an antifungal reagent, and wherein the antifungal reagent is selected from the group consisting of Polyene anti fungal, Imidazole, Triazole, Thiazole, Echinocandin, Aurone, Benzoic acid, Ciclopirox, Flucytosine and 5-fluorocytosine, Griseofulvin, Haloprogin, Tolnaftate, Undecylenic acid, Crystal violet, Balsam of Peru, an analog thereof, a salt thereof, and a derivative thereof.

\* \* \* \* \*